(12) United States Patent
Ozsolak

(10) Patent No.: US 10,041,074 B2
(45) Date of Patent: Aug. 7, 2018

(54) EUCHROMATIC REGION TARGETING METHODS FOR MODULATING GENE EXPRESSION

(71) Applicant: Translate Bio MA, Inc., Lexington, MA (US)

(72) Inventor: Fatih Ozsolak, Boston, MA (US)

(73) Assignee: Translate Bio MA, Inc., Lexington, MA (US)

( * ) Notice: Subject to any disclaimer, the term of this patent is extended or adjusted under 35 U.S.C. 154(b) by 0 days.

(21) Appl. No.: 14/700,269

(22) Filed: Apr. 30, 2015

(65) Prior Publication Data

US 2015/0232858 A1    Aug. 20, 2015

Related U.S. Application Data

(63) Continuation of application No. PCT/US2014/051265, filed on Aug. 15, 2014.

(60) Provisional application No. 61/866,772, filed on Aug. 16, 2013.

(51) Int. Cl.
C07H 21/04     (2006.01)
C12N 15/113    (2010.01)

(52) U.S. Cl.
CPC ...... *C12N 15/1137* (2013.01); *C12N 2310/11* (2013.01); *C12N 2310/321* (2013.01); *C12N 2310/3231* (2013.01); *C12N 2320/30* (2013.01)

(58) Field of Classification Search
None
See application file for complete search history.

(56) References Cited

U.S. PATENT DOCUMENTS

| | | |
|---|---|---|
| 4,725,677 A | 2/1988 | Köster et al. |
| 5,919,619 A | 7/1999 | Tullis |
| 6,294,650 B1 | 9/2001 | Shay et al. |
| 6,451,991 B1 | 9/2002 | Martin et al. |
| 6,858,726 B2 | 2/2005 | Koch et al. |
| 6,919,439 B2 | 7/2005 | Manoharan et al. |
| 7,041,816 B2 | 5/2006 | Ravikumar et al. |
| 7,683,036 B2 | 3/2010 | Esau et al. |
| 7,790,675 B2 | 9/2010 | Scheiber-Mojdehkar et al. |
| 7,858,592 B2 | 12/2010 | Shames et al. |
| 8,067,569 B2 | 11/2011 | Iversen et al. |
| 8,153,606 B2 | 4/2012 | Collard et al. |
| 9,593,330 B2 | 3/2017 | Collard et al. |
| 2005/0054836 A1 | 3/2005 | Krainer et al. |
| 2005/0079614 A1 | 4/2005 | Reinhart et al. |
| 2007/0219244 A1 | 9/2007 | Jenssen et al. |
| 2008/0015162 A1 | 1/2008 | Bhanot et al. |
| 2009/0082297 A1 | 3/2009 | Lioy et al. |
| 2009/0092988 A1 | 4/2009 | Schwartz et al. |
| 2009/0325868 A1 | 12/2009 | Liu et al. |
| 2010/0105760 A1* | 4/2010 | Collard ............ C07K 14/775 514/44 A |
| 2010/0285476 A1 | 11/2010 | Rusche et al. |
| 2011/0054012 A1 | 3/2011 | Place et al. |
| 2011/0294226 A1 | 12/2011 | Melki et al. |
| 2012/0004278 A1 | 1/2012 | Chang et al. |
| 2012/0149759 A1 | 6/2012 | Collard et al. |
| 2012/0171170 A1 | 7/2012 | Collard et al. |
| 2012/0190728 A1 | 7/2012 | Bennett et al. |
| 2012/0295952 A1 | 11/2012 | Collard et al. |
| 2013/0164846 A1 | 6/2013 | Saestrom |
| 2013/0210918 A1 | 8/2013 | Gottesfeld et al. |
| 2013/0225659 A1 | 8/2013 | Bennett |
| 2014/0187606 A1 | 7/2014 | Collard et al. |
| 2015/0050738 A1 | 2/2015 | Ozsolak et al. |
| 2015/0225722 A1 | 4/2015 | Ozsolak |
| 2016/0201063 A1 | 7/2016 | Ozsolak |
| 2016/0201064 A1 | 7/2016 | Ozsolak |

FOREIGN PATENT DOCUMENTS

| | | |
|---|---|---|
| WO | WO 95/33852 A1 | 12/1995 |
| WO | WO 02/096923 A1 | 12/2002 |
| WO | WO 2008/018795 | 2/2008 |
| WO | WO 2009/024781 A1 | 2/2009 |
| WO | WO 2009/055675 | 4/2009 |
| WO | WO 2010/093860 A2 | 8/2010 |
| WO | WO 2011/097388 A1 | 8/2011 |
| WO | WO 2012/012443 A2 | 1/2012 |
| WO | WO 2012/024478 A2 | 2/2012 |
| WO | WO 2012/028961 A2 | 3/2012 |
| WO | WO 2012/044171 A1 | 4/2012 |
| WO | WO 2012/138289 A1 | 10/2012 |
| WO | WO 2012/149478 A2 | 11/2012 |
| WO | WO 2012/162514 A2 | 11/2012 |
| WO | WO 2012/174610 A1 | 12/2012 |
| WO | WO 2013/040429 | 3/2013 |
| WO | WO 2013/120003 A1 | 8/2013 |
| WO | WO 2013/173598 | 11/2013 |
| WO | WO 2013/173601 | 11/2013 |
| WO | WO 2013/173608 | 11/2013 |
| WO | WO 2013/173635 | 11/2013 |
| WO | WO 2013/173647 | 11/2013 |
| WO | WO 2013/173652 | 11/2013 |
| WO | WO 2014/043544 | 3/2014 |
| WO | WO 2014/197826 | 12/2014 |
| WO | WO 2015/020993 A2 | 2/2015 |
| WO | WO 2015/023975 | 2/2015 |

OTHER PUBLICATIONS

Fish et al (J. Biol. Chem. 282(21): 15652-15666, 2007).*
Laumonnier et al (J. Biol. Chem. 275(52): 40732-40471, 2000).*
Fish et al (J. Biol. Chem. 280(26): 24824-24838, 2005).*
Halley et al (Cell Reports 6, 222-230, Jan. 16, 2014).*
Moderresi et al (Nature Biotech 30(5): 453-459, 2012), including "Online Methods" (2 pages attached to the journal article).*
Supplemental Online Materials for Moderresi et al (Nature Biotech 30(5): 453-459, 2012), 33 pages.*
Ebralidze et al (Genes & Development 22:2085-2092, 2008).*
Supplemental Data, 43 pages, from Ebralidze et al (Genes & Development 22:2085-2092, 2008).*

(Continued)

*Primary Examiner* — Richard A Schnizer
(74) *Attorney, Agent, or Firm* — Wolf, Greenfield & Sacks, P.C.

(57) ABSTRACT

Provided herein are oligonucleotides complementary to euchromatic regions of target genes that are useful for increasing expression of the target genes; related compositions and methods are also provided.

13 Claims, 17 Drawing Sheets

(56) References Cited

OTHER PUBLICATIONS

Yang et al (Endocrinology 144(12):5658-5670, 2003).*
Halley et al (Drug Discov Today Ther Strateg. 10(3): e119-e125, May 10, 2013).*
Sun et al (Nucl. Acids Res., 33(17): 5533-5543, 2005).*
Wang et al (PLoS ONE 7(8): e42414, 2012).*
"A User's Guide to the Encyclopedia of DNA Elements (ENCODE)", The ENCODE Project Consortium, (PLoS Biology 9(4): e1001046, 2011).*
Genbank Submission; NIH/NCBI, Accession No. AL137002. Holt, Dec. 13, 2012. 29 pages.
Daughters et al., RNA gain-of-function in spinocerebellar ataxia type 8. PLoS Genet. Aug. 2009;5(8):e1000600. doi: 10.1371/journal.pgen.1000600. Epub Aug. 14, 2009.
Dominski et al., Identification and characterization by antisense oligonucleotides of exon and intron sequences required for splicing. Mol Cell Biol. Nov. 1994; 14(11): 7445-7454.
Dominski et al., Restoration of correct splicing in thalassemic pre-mRNA by antisense oligonucleotides. Proc Natl Acad Sci U S A. Sep. 15, 1993;90(18):8673-7.
Jepsen et al., Locked nucleic acid: a potent nucleic acid analog in therapeutics and biotechnology. Oligonucleotides. 2004;14(2):130-46. Review.
Johnson, Long non-coding RNAs in Huntington's disease neurodegeneration. Neurobiol Dis. 2012;46:245-54.
Munroe, Antisense RNA inhibits splicing of pre-mRNA in vitro. EMBO J. Aug. 1988; 7(8):2523-32.
Ozsolak et al., Comprehensive polyadenylation site maps in yeast and human reveal pervasive alternative polyadenylation. Cell. Dec. 10, 2010;143(6):1018-29. doi: 10.1016/j.cell.2010.11.020.
Rigo et al., Antisense-based therapy for the treatment of spinal muscular atrophy. J Cell Biol. Oct. 1, 2012;199(1):21-5. doi: 10.1083/jcb.201207087.
Sun et al., Characterization of Xpr (Xpct) reveals instability but no effects on X-chromosome pairing or Xist expression. Transcription. 2010;1:46-56.
Wutz et al., Chromosomal silencing and localization are mediated by different domains of Xist RNA. Nat Genet. Feb. 2002;30(2):167-74.
Genbank Submission; NCBI, Accession No. U93173.1; Laccone et al., Jan. 5, 1999.
Genbank Submission; NCBI, Accession No. NG_011794.1; Rosenfeld et al. Oct. 6, 2016.
Boyle et al., High-resolution mapping and characterization of open chromatin across the genome. Cell. Jan. 25, 2008;132(2):311-22. doi:10.1016/j.cell.2007.12.014.
Crawford et al., Genome-wide mapping of DNase hypersensitive sites using massively parallel signature sequencing (MPSS). Genome Res. Jan. 2006;16(1):123-31.
Li et al., Excision of Expanded GAA Repeats Alleviates the Molecular Phenotype of Friedreich's Ataxia. Mol Ther. Jun. 2015;23(6):1055-65. doi:10.1038/mt.2015.41. Epub Mar. 11, 2015.
Song et al., Open chromatin defined by DNaseI and FAIRE identifies regulatory elements that shape cell-type identity. Genome Res. Oct. 2011;21(10):1757-67. doi: 10.1101/gr.121541.111.
Encode Project Consortium. A user's guide to the encyclopedia of DNA elements (Encode). PLoS Biol. Apr. 2011;9(4):e1001046. doi: 10.1371/journal.pbio.1001046. Epub Apr. 19, 2011.
Geneseq Submission; EBI Accession No. AJL53182. Dec. 28, 2007.
Geneseq Submission; EBI Accession No. AXQ92558. Nov. 26, 2009.
Geneseq Submission; EBI Accession No. AJJ96000. Dec. 28, 2007.
Geneseq Submission; EBI Accession No. AYB40768. Jul. 22, 2010.
Wang et al., Correlation between Dnase I hypersensitive site distribution and gene expression in HeLa S3 cells. PLoS One. 2012;7(8):e42414. doi: 10.1371/journal.pone.0042414. Epub Aug. 10, 2012.
Xu et al., Improved Histone Deacetylase Inhibitors as Therapeutics for the Neurodegenerative Disease Friedreich's Ataxia: A New Synthetic Route. Pharmaceuticals (Basel). Dec. 14, 2011;4(12):1578-1590.
International Search Report and Written Opinion for PCT/US2014/051265 dated Nov. 26, 2014.
Genbank Submission; NIH/NCBI, Accession No. NM_001079668. Young et al., Jan. 18, 2014. 4 pages.
Genbank Submission; NIH/NCBI, Accession No. XM_004398354. 1. Mar. 31, 2013. 2 pages.
Ahn et al., Retinoic acid accelerates downregulation of the Xist repressor, Oct. 4, and increases the likelihood of Xist activation when Tsix is deficient. BMC Develop Biol. 2010;10:90. 14 pages.
Bernstein et al., A bivalent chromatin structure marks key developmental genes in embryonic stem cells. Cell. Apr. 21, 2006;125(2):315-26.
Bernstein et al., Mouse polycomb proteins bind differentially to methylated histone H3 and RNA and are enriched in facultative heterochromatin. Mol Cell Biol. Apr. 2006;26(7):2560-9.
Bernstein et al., RNA meets chromatin. Genes Dev. Jul. 15, 2005;19(14):1635-55. Review.
Chan et al., Heterochromatinization induced by GAA-repeat hyperexpansion in Friedreich's ataxia can be reduced upon HDAC inhibition by vitamin B3. Hum Mol Genet. 2013;22(13):2662-75.
Greiner et al., Identification of a specific inhibitor of the histone methyltransferase SU(VAR)3-9. Nature Chem Biol. Aug. 2005;1(3):143-5.
Jeon et al., YY1 tethers Xist RNA to the inactive X nucleation center. Cell. Jul. 8, 2011;146(1):119-33. doi: 10.1016/j.cell.2011.06.026.
Kanhere et al., Short RNAs are transcribed from repressed polycomb target genes and interact with polycomb repressive complex-2. Mol Cell. Jun. 11, 2010;38(5):675-88. doi: 10.1016/j.molcel.2010.03.019.
Kubiura et al., Chromosome-wide regulation of euchromatin-specific 5mC to 5hmC conversion in mouse ES cells and female human somatic cells. Chromosome Res. Oct. 2012;20(7):837-48. doi: 10.1007/s10577-012-9317-9. Epub Oct. 31, 2012.
Lee, Epigenetic regulation by long noncoding RNAs. Science. Dec. 14, 2012;338(6113):1435-9. Review.
Li et al., Expression of human frataxin is regulated by transcription factors SRF and TFAP2. PLoS One. Aug. 20, 2010;5(8):e12286. doi: 10.1371/journal.pone.0012286. 8 pages.
Mikkelsen et al., Genome-wide maps of chromatin state in pluripotent and lineage-committed cells. Nature. Aug. 2, 2007;448(7153):553-60. doi:10.1038/nature06008. Epub Aug. 13, 2010. 21 pages.
Miller et al., A Tale nuclease architecture for efficient genome editing. Nat Biotechnol. Feb. 2011;29(2):143-8. doi: 10.1038/nbt.1755. Epub Dec. 22, 2010.
Miremadi et al., Cancer genetics of epigenetic genes. Hum Mol Genet. Apr. 15, 2007;16 Spec No. 1:R28-49. Review.
Nagano et al., The Air noncoding RNA epigenetically silences transcription by targeting G9a to chromatin. Science. Dec. 12, 2008;322(5908):1717-20.
Pereira et al., Ezh2, the histone methyltransferase of PRC2, regulates the balance between self-renewal and differentiation in the cerebral cortex. Proc Natl Acad Sci U S A. Sep. 7, 2010;107(36):15957-62. doi: 10.1073/pnas.1002530107. Epub Aug. 23, 2010.
Reyon et al., FLASH assembly of TALENs for high-throughput genome editing. Nat Biotechnol. May 2012;30(5):460-5. doi: 10.1038/nbt.2170.
Sankaran, Targeted therapeutic strategies for fetal hemoglobin induction. Hematology Am Soc Hematol Educ Program. 2011;2011:459-65.
Slawson et al., Comparison of dot chromosome sequences from D. melanogaster and D. virilis reveals an enrichment of DNA transposon sequences in heterochromatic domains. Genome Biol. 2006;7(2):R15. Epub Feb. 20, 2006. 18 pages.
Wang et al., Molecular mechanisms of long noncoding RNAs. Cell Press. Sep. 16, 2011; 43(6):904-14.

(56) References Cited

OTHER PUBLICATIONS

Wassenegger et al., RNA-Directed De Novo Methylation of Genomic Sequences in Plants. Cell. Feb. 11, 1994;76:567-76.
Yandim et al., Gene regulation and epigenetics in Friedreich's ataxia. J Neurochem. Aug. 2013;126 Suppl 1:21-42. doi: 10.1111/jnc.12254. Review.
Ditch et al., Progressive GAA.TTC repeat expansion in human cell lines. PLoS Genet. Oct. 2009;5(10):e1000704. doi: 10.1371/journal.pgen.1000704.
Genbank Submission; NCBI, Accession No. NM_181897.2. Oct. 16, 2017.
Genbank Submission; NCBI, Accession No. NM_002605.2. Oct. 16, 2017.
Bandiera et al., Genetic variations creating microRNA target sites in the FXN 3'-UTR affect frataxin expression in Friedreich ataxia. PLoS One. 2013;8(1):e54791. doi: 10.1371/journal.pone.0054791. Epub Jan. 30, 2013.

* cited by examiner

EUCHROMATIC REGION TARGETING METHODS FOR MODULATING GENE EXPRESSION

CROSS-REFERENCE TO RELATED APPLICATIONS

This application is a continuation of International Patent Application Serial No. PCT/US2014/051265, filed Aug. 15, 2014 which claims the benefit under 35 U.S.C. § 119(e) of U.S. Provisional Application No. 61/866,772, entitled "OLIGONUCLEOTIDES TARGETING EUCHROMATIN REGIONS OF GENES", filed Aug. 16, 2013, the contents of each of which are incorporated herein by reference in their entirety.

FIELD OF THE INVENTION

The invention relates in part to oligonucleotide based compositions, as well as methods of using oligonucleotide based compositions to modulate gene expression.

BACKGROUND OF THE INVENTION

A considerable portion of human diseases can be treated by selectively altering protein and/or RNA levels of disease-associated transcription units (noncoding RNAs, protein-coding RNAs or other regulatory coding or noncoding genomic regions). Such methods may involve blocking translation of mRNAs or causing degradation of target RNAs. However, additional approaches for modulating gene expression are desirable, especially with regard to increasing expression levels as limited approaches are available for increasing the expression of genes.

SUMMARY OF THE INVENTION

According to some aspects of the invention, methods and compositions are provided herein that are useful for increasing gene expression in a targeted and specific manner. Aspects of the invention are based on the identification of euchromatic regions of genes that overlap with sequences encoding antisense RNA transcripts. It has been found that oligonucleotides that are complementary to these particular euchromatic regions of target genes are useful for increasing expression of target genes when delivered to cells. In some embodiments, oligonucleotides are provided that are complementary with these euchromatic regions and that have chemistries suitable for delivery, hybridization and stability within cells. Furthermore, in some embodiments, oligonucleotide chemistries are provided that are useful for controlling the pharmacokinetics, biodistribution, bioavailability and/or efficacy of the oligonucleotides in vivo. Accordingly, in some embodiments, oligonucleotides provided herein are useful for the treatment of diseases or conditions associated with decreased levels of target genes.

Accordingly, in some aspects of the invention, oligonucleotides are provided that are useful for increasing expression of a target gene. In some embodiments, the oligonucleotides are 10 to 50 nucleotides in length and have a region of complementarity that is complementary with at least 5 contiguous nucleotides in a euchromatic region of a target gene. In some embodiments, the antisense strand of the target gene comprises, in the euchromatic region, a nucleotide sequence that encodes at least a portion of an RNA transcript. In certain embodiments, the portion of the RNA transcript encoded in the euchromatic region comprises the first transcribed nucleotide at the 5'-end of the RNA transcript. In some embodiments, the at least 5 contiguous nucleotides in the euchromatin region are on the sense strand of the target gene. In certain embodiments, the at least 5 contiguous nucleotides in the euchromatin region are on the antisense strand of the target gene. In some embodiments, the RNA transcript is a long non-coding RNA, miRNA, piRNA, snRNA, eRNAs or snoRNA or any other suitable RNA transcript.

In some embodiments, the euchromatic region of the target gene is a region that is hypersensitive to DNAseI or micrococcal nuclease compared to an appropriate control. In certain embodiments, the euchromatic region of the target gene is enriched in a methylated histone (e.g., lysine 4 methylated histone H3 or H4) compared to an appropriate control. In some embodiments, the euchromatic region of the target gene is enriched in an acetylated histone (e.g., an acetylated histone H3 or H4) compared to an appropriate control.

In certain embodiments, the sense strand of the target gene encodes a messenger RNA. In some embodiments, in the euchromatic region, the sense strand of the target gene comprises a nucleotide sequence that encodes a UTR of the messenger RNA. In certain embodiments, in the euchromatic region, the sense strand of the target gene comprises a nucleotide sequence that encodes at least a portion of an intron of the messenger RNA. In some embodiments, in the euchromatic region, the sense strand of the target gene comprises a nucleotide sequence that encodes at least a portion of an exon of the messenger RNA. In certain embodiments, the sense strand of the target gene encodes a non-coding RNA.

In certain embodiments, the oligonucleotide is a single stranded oligonucleotide. In some embodiments, the oligonucleotide comprises at least one modified intranucleoside linkage. In certain embodiments, the oligonucleotide comprises at least one modified nucleotide. In some embodiments, at least one nucleotide of the oligonucleotide comprises a 2' O-methyl. In certain embodiments, the oligonucleotide comprises at least one ribonucleotide, at least one deoxyribonucleotide, at least one 2'-fluoro-deoxyribonucleotide or at least one bridged nucleotide. In some embodiments, the bridged nucleotide is a LNA nucleotide, a cEt nucleotide or a ENA modified nucleotide. In certain embodiments, each nucleotide of the oligonucleotide is a LNA nucleotide. In some embodiments, the oligonucleotide is mixmer. In certain embodiments, the nucleotides of the oligonucleotide comprise alternating deoxyribonucleotides and 2'-fluoro-deoxyribonucleotides, 2'-O-methyl nucleotides, or bridged nucleotides. In some embodiments, the oligonucleotide is a gapmer.

In certain embodiments, the target gene is selected from the group consisting of: ABCA1, APOA1, ATP2A2, BDNF, FXN, HBA2, HBB, HBD, HBE1, HBG1, HBG2, SMN, UTRN, PTEN, MECP2, and FOXP3. In some embodiments, the target gene is selected from the group consisting of: ABCA4, ABCB11, ABCB4, ABCG5, ABCG8, ADIPOQ, ALB, APOE, BCL2L11, BRCA1, CD274, CEP290, CFTR, EPO, F7, F8, FLI1, FMR1, FNDC5, GCH1, GCK, GLP1R, GRN, HAMP, HPRT1, IDO1, IGF1, IL10, IL6, KCNMA1, KCNMB1, KCNMB2, KCNMB3, KCNMB4, KLF1, KLF4, LDLR, MSX2, MYBPC3, NANOG, NF1, NKX2-1, NKX2-1-AS1, PAH, PTGS2, RB1, RPS14, RPS19, SCARB1, SERPINF1, SIRT1, SIRT6, SMAD7, ST7, STAT3, TSIX, and XIST.

In certain embodiments, oligonucleotides are provided that comprise a nucleotide sequence as set forth in Table 3 or Table 6.

In some aspects of the invention, oligonucleotides are provided that have a region of complementarity that is complementary with at least 5 contiguous nucleotides in a euchromatic region of a target gene, in which the sense strand of the target gene comprises a nucleotide sequence that encodes a first RNA transcript and in which the antisense strand of the target gene comprises, in the euchromatic region, a nucleotide sequence that encodes a nucleotide sequence of a second RNA transcript. In some embodiments, the first RNA transcript is an mRNA transcript. In some embodiments, the first RNA transcript is a functional RNA transcript (e.g., an rRNA, a tRNA, a miRNA, etc.) In some embodiments, the second RNA transcript is a non-coding RNA transcript.

In some aspects of the invention, methods are provided for increasing expression of a target gene in a cell. In some embodiments, the methods involve contacting a cell with any one or more of the oligonucleotides disclosed herein that are useful for increasing expression of a target gene in a cell. In some embodiments, the cell is in vitro. In some embodiments, the cell is in vivo. In other aspects of the invention, methods are provided for treating a condition associated with insufficient levels of expression of a target gene in a subject in need thereof. In some embodiments, the methods involve administering to the subject an effective amount of any one or more of the oligonucleotides disclosed herein that are useful for increasing expression of a target gene.

In some aspects of the invention, compositions are provided that comprise one or more oligonucleotides disclosed herein. In some embodiments, the oligonucleotide is complexed with a monovalent cation (e.g., Li+, Na+, K+, Cs+). In some embodiments, the oligonucleotide is in a lyophilized form. In some embodiments, the oligonucleotide is in an aqueous solution. In some embodiments, the oligonucleotide is provided, combined or mixed with a carrier (e.g., a pharmaceutically acceptable carrier). In some embodiments, the oligonucleotide is provided in a buffered solution. In some embodiments, the oligonucleotide is conjugated to a carrier. In some aspects of the invention, kits are provided that comprise a container housing the composition.

In some aspects of the invention, methods are provided for producing a candidate oligonucleotide for increasing expression of a target gene. In some embodiments, the methods involve one or more of the following steps (a) determining a location of a euchromatic region in a target gene; (b) determining a location of a nucleotide sequence in the euchromatic region on the antisense strand of the target gene that encodes an RNA transcript; and (c) producing an oligonucleotide of 10 to 50 nucleotides in length that has a region of complementarity that is complementary with at least 5 contiguous nucleotides in the euchromatic region of the target gene.

In some aspects of the invention, methods are provided for obtaining one or more oligonucleotides for increasing expression of a target gene. In some embodiments, the methods involve one or more of the following steps (a) determining a location of a euchromatic region in a target gene; (b) determining a location of a nucleotide sequence in the euchromatic region on the antisense strand of the target gene that encodes an RNA transcript; (c) producing a plurality of different oligonucleotides of 10 to 50 nucleotides in length, in which each oligonucleotide has a region of complementarity that is complementary with at least 5 contiguous nucleotides in the euchromatic region of the target gene; (d) subjecting each of the different oligonucleotides to an assay that assesses whether delivery of an oligonucleotide to a cell harboring the target gene results in increased expression of the target gene in the cell; and (e) obtaining one or more oligonucleotides that are identified based on the results in (d) as increasing expression of the target gene.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION OF THE INVENTION

Figure 1:
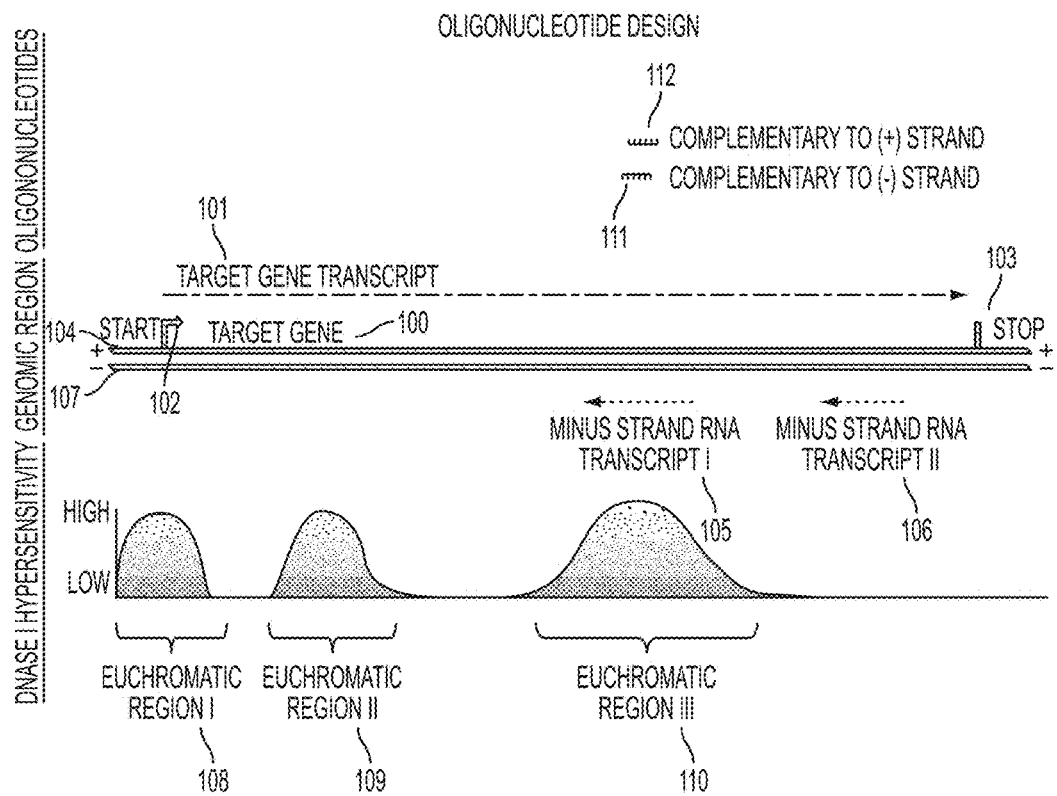
FIG. 1 is a diagram showing a design scheme for oligonucleotides that are complementary to a target euchromatic region.

Aspects of the invention relate to compositions and methods for increasing expression of genes. In some embodiments, the invention relates to the discovery of certain euchromatic regions within or associated with genes that may be targeted to increase expression of the genes. In some embodiments, these targeted euchromatic regions contain nucleotide sequences, on the antisense strand of genes, from which are transcribed antisense RNA transcripts that are believed to inhibit expression of the genes. Without wishing to be bound by theory, in some embodiments, it is believed that these antisense strand RNA transcripts may disrupt transcription, processing, maturation and/or function of RNA transcripts encoded in the sense strands of the genes. Accordingly, in some embodiments, it is believed that use of oligonucleotides that block the function of these antisense transcripts can restore transcription, processing, maturation and/or function of the corresponding sense RNA transcripts.

As used herein, the term, "euchromatic region" refers to a genomic region enriched in open chromatin. In some embodiments, a euchromatic region is a genomic region that is hypersensitive to nuclease digestion, e.g., by DNAseI or micrococcal nuclease. Thus, in some embodiments, euchromatic regions may be identified using DNase-Seq (DNase I hypersensitive sites sequencing), which is based on sequencing of regions sensitive to cleavage by DNase I.

In some embodiments, a euchromatic region is a genomic region that is relatively depleted of nucleosomes. Thus, in some embodiments, euchromatic regions may be identified using FAIRE-Seq (Formaldehyde-Assisted Isolation of Regulatory Elements), which is based on an observation that formaldehyde cross-linking is more efficient in nucleosome-bound DNA than it is in nucleosome-depleted regions of the genome. This method segregates the non-cross-linked DNA that is usually found in open chromatin, which is then sequenced. The protocol typically involves cross linking, phenol extraction and sequencing DNA in aqueous phase.

In some embodiments, a euchromatic region is a genomic region that is enriched in methylated histones (e.g., methylated Histone H1, H2A, H2B, H3 or H4) compared to an appropriate control. In some embodiments, an appropriate control is a corresponding genomic region in a cell, tissue or fluid obtained from a healthy subject or population of healthy subjects. As used herein, a healthy subject is a subject that is apparently free of disease and has no history of disease, e.g., no history of Friedreich's ataxia or another disease described herein. In some embodiments, an appropriate control is a corresponding genomic region in a cell from a subject that does not have Friedreich's ataxia or is a corresponding genomic region in a population of cells from a population of subjects that do not have Friedreich's ataxia. In some embodiments, the subject or population of subjects that do not have Friedreich's ataxia are subjects that have a FXN gene that contains less than 20, 19, 18, 17, 16, 15, 14, 13, 12, 11, or 10 GAA repeat units in the first intron. In some embodiments, a euchromatic region is a genomic region that is enriched in histone H3 that is monomethylated or trimethylated at lysine 4. In some embodiments, a euchromatic region is a genomic region that is enriched in histone H3 that is trimethylated at lysine 36. In some embodiments, a euchromatic region is a genomic region that is enriched in histone H3 that is monomethylated at lysine 9, lysine 27 or lysine 79. In some embodiments, a euchromatic region is a genomic region that is enriched in histone H3 that is dimethylated or trimethylated at lysine 79. In some embodiments, a euchromatic region is a genomic region that is enriched in histone H4 that is monomethylated at lysine 20. In some embodiments, a euchromatic region is a genomic region that is enriched in histone H2B that is monomethylated at lysine 5. In some embodiments, a euchromatic region is a genomic region that is enriched in acetylated histones (e.g., acetylated Histone H1, H2A, H2B, H3 or H4) compared to an appropriate control. In some embodiments, a euchromatic region is a genomic region that is enriched in Histone H3 that is acetylated at lysine 9, lysine 14 or lysine 27.

Other modifications of histones may be used to identify euchromatic regions including, for example, phosphorylation, ubiquitination, SUMOylation, citrullination, and ADP-ribosylation of histone tails.

In some embodiments, information obtained through nucleosome mapping may be used to identify regulatory regions (e.g., euchromatic regions). In some embodiments, euchromatic regions are nucleosome-depleted compared with other genomic regions (e.g., heterochromatic regions).

Further methods for identifying open chromatin are available and include, for example, methods described in Boyle, A. P. et al., *High-Resolution Mapping and Characterization of Open Chromatin across the Genome*. Cell, Volume 132, Issue 2, 311-322, 25 Jan. 2008; Song L, et al., *Open chromatin defined by DNaseI and FAIRE identifies regulatory elements that shape cell-type identity*. Genome Res. 2011 October; 21(10):1757-67; and Crawford G E, et al., *Genome-wide mapping of DNase hypersensitive sites using massively parallel signature sequencing (MPSS)*. Genome Res. 2006 January; 16(1):123-31; the contents of each of which are incorporated herein by reference in their entireties.

Information regarding the location of euchromatic regions may also be found in the UCSC genome browser and other public databases. For example, the Encyclopedia of DNA Elements (ENCODE) Consortium Analysis Working Group (AWG) has performed uniform processing on datasets produced by multiple data production groups in the ENCODE Consortium, and UCSC has released browser tracks based on the AWG uniform processing of ENCODE DNaseI data. Data in UCSC can be represented as either raw reads or processed locations of DNAseI hypersensitive locations. For example, UCSC genome browser provides DNaseI Hypersensitivity Uniform Peaks from ENCODE/Analysis, which is a track that displays a set of open chromatin elements in multiple different cell types on a per-cell type basis. UCSC genome browser also provides Digital DNaseI Hypersensitivity Clusters in cell types from ENCODE, which displays clusters of Uniform DNaseI Hypersensitive sites across the cell types assayed. Genomic region enriched in open chromatin can thus be identified using this information.

Euchromatic regions may be in any region within or associated with a target gene. For example, a euchromatic region may map to a position in a target gene that comprises a nucleotide sequence that encodes a UTR, or portion thereof, of a messenger RNA. In another example, a euchromatic region may map to a position in a target gene that comprises a nucleotide sequence that encodes at least a portion of an intron of a messenger RNA. In another example, a euchromatic region may map to a position in a target gene that comprises a nucleotide sequence that encodes at least a portion of an exon of a messenger RNA. In another example, a euchromatic region may map to a position in a target gene that comprises a nucleotide sequence that encodes an intron-exon boundary.

In some embodiments, a euchromatic region does not comprise a nucleotide sequence that encodes an intron, or portion thereof. In some embodiments, a euchromatic region does not comprise a nucleotide sequence that encodes an exon, or portion thereof. In some embodiments, a euchromatic region does not comprise a nucleotide sequence that encodes a 5'-UTR, or portion thereof. In some embodiments, a euchromatic region does not comprise a nucleotide sequence that encodes a 3'-UTR, or portion thereof. In some embodiments, a euchromatic region does not comprise a nucleotide sequence that encodes a promoter, enhancer or silencer, or portion other either one of them.

Euchromatic regions may be any length as determined by the size of open chromatin in a particular region of a target gene. In some embodiments, a euchromatic region is up to 50 base pairs, up to 100 base pairs, up to 200 base pairs, up to 500 base pairs, up to 1000 base pairs, up to 2000 base pairs, up to 5000 base pairs, or more in length. In some embodiments, a euchromatic region is 50 to 100 base pairs, 50 to 500 base pairs, 100 to 1000 base pairs, 100 to 2000 base pairs, 500 to 5000 base pairs, or more in length.

In some embodiments, oligonucleotides are provided that are complementary with a portion of a euchromatic region of a gene, in which the antisense strand of the gene comprises, in the euchromatic region, a nucleotide sequence that encodes at least portion of an RNA transcript (e.g., an antisense RNA transcript). In some embodiments, the oligonucleotides inhibit the function of antisense RNA transcripts that contain sequences transcribed from euchromatic regions in genes. Such oligonucleotides may be complementary with sequences on the sense or antisense strand of the gene. Accordingly, in some embodiments, the oligonucleotides may hybridize with the sense or antisense RNA transcript, in either case inhibiting or preventing the two transcripts from hybridizing within one another. In some embodiments, when oligonucleotides are complementary with an antisense transcript that has sequences transcribed from euchromatic regions in a gene, the oligonucleotides may inhibit the function of the antisense transcript by hybridizing to it and causing it to be degraded. Accordingly, in some embodiments, oligonucleotides are provided that cause degradation of an antisense RNA transcript resulting in increased expression of a corresponding sense RNA transcript of a target gene. However, in some embodiments, oligonucleotides are provided that inhibit hybridization of an antisense RNA transcript with a sense RNA transcript of a target gene, effectively resulting in increased expression of the target gene. And, in some embodiments, oligonucleotides are provided that inhibit function of a gene in a manner that does not involve targeting of an RNA transcript. In some embodiments, oligonucleotides are provided that bind to DNA at a euchromatic region and disrupt protein-DNA interactions at the euchromatic region (e.g., by dislocating a transcription factor or other factor binding to the DNA, etc.).

In some embodiments, if a sense RNA transcript expressed from a target gene is a mRNA transcript, use of an oligonucleotide provided herein results in increased levels of mRNA available for translation and thus increased levels of the translated protein. In some embodiments, if the sense RNA transcript expressed from the target gene is a non-coding RNA transcript (e.g., an miRNA, lncRNA), use of an oligonucleotide provided herein results in increased levels of the non-coding RNA transcript and thus increased activity of the non-coding RNA.

Any gene that has or is associated with a euchromatic region that overlaps with a sequence encoding an RNA transcript (e.g., an RNA transcript that is antisense to the gene) may be targeted using the compositions and methods disclosed herein. In some embodiments, the target gene is selected from the group consisting of: ABCA1, APOA1, ATP2A2, BDNF, FXN, HBA2, HBB, HBD, HBE1, HBG1, HBG2, SMN, UTRN, PTEN, MECP2, and FOXP3. In some embodiments, the target gene is ABCA4, ABCB11, ABCB4, ABCG5, ABCG8, ADIPOQ, ALB, APOE, BCL2L11, BRCA1, CD274, CEP290, CFTR, EPO, F7, F8, FLI1, FMR1, FNDC5, GCH1, GCK, GLP1R, GRN, HAMP, HPRT1, IDO1, IGF1, IL10, IL6, KCNMA1, KCNMB1, KCNMB2, KCNMB3, KCNMB4, KLF1, KLF4, LDLR, MSX2, MYBPC3, NANOG, NF1, NKX2-1, NKX2-1-AS1, PAH, PTGS2, RB1, RPS14, RPS19, SCARB1, SERPINF1, SIRT1, SIRT6, SMAD7, ST7, STATS, TSIX, and XIST. Euchromatic regions for these and other genes may be selected or identified experimentally or based on information in public databases such as the UCSC genome browsers and others.

Furthermore, non-limiting examples of antisense RNA transcripts that are encoded by sequences overlapping or contained within euchromatic regions include non-coding RNA transcripts, long non-coding RNA, miRNA transcripts, snoRNA, and others.

Oligonucleotide Targeting Euchromatin Regions that Overlap Antisense RNA Transcript Sites In some embodiments, methods are provided for producing candidate oligonucleotides for increasing expression of a target gene. Generally, the oligonucleotides are complementary to sequences within euchromatin regions that overlap or contain sequences encoding an RNA transcript that is antisense to the target gene. Typically, oligonucleotides are designed by determining a location of a euchromatic region in a target gene; determining a location of a nucleotide sequence in the euchromatic region on the antisense strand of the target gene that encodes an RNA transcript; and producing an oligonucleotide that has a region of complementarity that is complementary with a plurality of (e.g., at least 5) contiguous nucleotides in the euchromatic region of the target gene.

In some embodiments, methods are provided for obtaining one or more oligonucleotides for increasing expression of a target gene that further involve producing a plurality of different oligonucleotides, in which each oligonucleotide has a region of complementarity that is complementary with a plurality of (e.g., at least 5) contiguous nucleotides in a target euchromatic region of the target gene; subjecting each of the different oligonucleotides to an assay that assesses whether delivery of an oligonucleotide to a cell harboring the target gene results in increased expression of the target gene in the cell; and obtaining one or more oligonucleotides that increase expression of the target gene in the assay.

FIG. 1 depicts a non-limiting embodiment of a method for design oligonucleotides that increase expression of a target gene 100. As depicted, target gene 100 encodes a target gene transcript 101 (e.g., a messenger RNA transcript) having a start site 102 and a stop site 103. In this example, target gene transcript 101 is expressed from the plus strand 104 of the chromosome. However, the target gene could be expressed from either the plus or minus strand of a chromosome. Also depicted are two RNA transcripts, 105, 106, that are expressed from the minus strand 107 of the chromosome within a region bounded by the start site 102 and stop site 103 encoded in the target gene 100.

Because the two RNA transcripts, 105, 106, are expressed from the minus strand 107 and the target gene transcript 101 is encoded on the plus strand 104, the two RNA transcripts, 105, 106, are antisense relative to the target gene 100. It will be appreciated that if a target gene target is encoded on the minus strand, then RNA transcripts which are antisense to the target gene will be expressed from the plus strand.

Three euchromatic regions 108, 109, 110, are present in the target gene 100, two of which euchromatic regions, 109, 110, are completely encompassed within the region bounded by the start site 102 and stop site 103. In this example, candidate oligonucleotides for increasing expression of the target gene 100 are designed against the euchromatic region 110 that overlaps the region from which is expressed minus strand RNA transcript 106. One candidate oligonucleotide is complementary to the minus strand 111 and the other candidate oligonucleotide 112 is complementary to the plus strand. Other similar candidate oligonucleotides may be designed.

It should be appreciated that target euchromatic regions need not be completely encompassed within a region bounded by start and stop sites of a target gene, provided that they comprise a sequence that overlaps with a region from which is expressed RNA transcript that is antisense to a target gene.

Oligonucleotides for Increasing Gene Expression

In one aspect, the invention relates to methods for increasing gene expression in a cell for research purposes (e.g., to study the function of the gene in the cell). In another aspect, the invention relates to methods for increasing gene expression in a cell for therapeutic purposes. The cells can be in vitro, ex vivo, or in vivo (e.g., in a subject in need thereof, such a as a subject who has a disease resulting from reduced expression or activity of a target gene). In some embodiments, methods for increasing gene expression in a cell comprise delivering an oligonucleotide as described herein. In some embodiments, gene expression is increased compared to an appropriate control. In some embodiments, gene expression is increased by at least 5%, 10%, 20%, 30%, 40%, 50%, 60%, 70%, 80%, 90%, 100%, 200%, 300%, 400%, 500% or more compared to an appropriate control. In some embodiments, an appropriate control is control level of gene expression. In some embodiments, an appropriate control may be a control level of gene expression in a cell, tissue, or subject to which an oligonucleotide has not been delivered or to which a negative control has been delivered (e.g., a scrambled oligo, a carrier, etc.).

It is understood that any reference to uses of compounds throughout the description contemplates use of the compound in preparation of a pharmaceutical composition or medicament for use in the treatment of condition or a disease. Thus, as one non-limiting example, this aspect of the invention includes use of such oligonucleotides in the preparation of a medicament for use in the treatment of disease. Table 1 listed examples of diseases or conditions that may be treated.

TABLE 1

Examples of diseases or conditions treatable with oligonucleotides targeting Euchromatic regions of particular target genes.

| Target Gene | Disease or Conditions |
|---|---|
| FXN | Friedreich's Ataxia |
| SMN | Spinal muscular atrophy (SMA) types I-IV |
| UTRN | Muscular dystrophy (MD) (e.g., Duchenne's muscular dystrophy, Becker's muscular dystrophy, myotonic dystrophy) |
| HEMOGLOBIN | Anemia, microcytic anemia, sickle cell anemia and/or thalassemia (e.g., alpha-thalassemia, beta-thalaseemia, delta-thalessemia), beta-thalaseemia (e.g., thalassemia minor/intermedia/major) |
| ATP2A2 | Cardiac conditions (e.g., congenital heart disease, aortic aneurysms, aortic dissections, arrhythmia, cardiomyopathy, and congestive heart failure), Darier-White disease and Acrokeratosis verruciformi |
| APOA1/ABCA1 | Dyslipidemia (e.g. Hyperlipidemia) and atherosclerosis (e.g. coronary artery disease (CAD) and myocardial infarction (MI)) |
| PTEN | Cancer, such as, leukemias, lymphomas, myelomas, carcinomas, metastatic carcinomas, sarcomas, adenomas, nervous system cancers and genito-urinary cancers. In some embodiments, the cancer is adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, or Wilms tumor |

TABLE 1-continued

Examples of diseases or conditions treatable with oligonucleotides targeting Euchromatic regions of particular target genes.

| Target Gene | Disease or Conditions |
|---|---|
| BDNF | Amyotrophic lateral sclerosis (ALS, also known as Lou Gehrig's disease), Alzheimer's Disease (AD), and Parkinson's Disease (PD), Neurodegeneration |
| MECP2 | Rett Syndrome, MECP2-related severe neonatal encephalopathy, Angelman syndrome, or PPM-X syndrome |
| FOXP3 | Diseases or disorders associated with aberrant immune cell (e.g., T cell) activation, e.g., autoimmune or inflammatory diseases or disorders. Examples of autoimmune diseases and disorders that may be treated according to the methods disclosed herein include, but are not limited to, Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, inflammatory bowel disease (e.g., Crohn's disease or Ulcerative colitis), Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, IPEX (Immunodysregulation, Polyendocrinopathy, and Enteropathy, X-linked) syndrome, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), systemic lupus erythematosus (SLE), chronic Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia , Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympatheticbophthalmia, Takayasu's arteritis, Temporal arteritis/Giant cell arteritis, Thrombocytopenic purpura (TTP), Tolosa-Hunt syndrome, Transverse myelitis, Type 1 diabetes, Undifferentiated connective tissue disease (UCTD), Uveitis, Vasculitis, Vesiculobullous dermatosis, Vitiligo, and Wegener's granulomatosis (also called Granulomatosis with Polyangiitis (GPA)). Further examples of autoimmune disease or disorder include inflammatory bowel disease (e.g., Crohn's disease or Ulcerative colitis), IPEX syndrome, Multiple sclerosis, Psoriasis, Rheumatoid arthritis, SLE or Type 1 diabetes. Examples of inflammatory diseases or disorders that may be treated according to the methods disclosed herein include, but are not limited to, Acne Vulgaris, Appendicitis, Arthritis, Asthma, Atherosclerosis, Allergies (Type 1 Hypersensitivity), Bursitis, Colitis, Chronic Prostatitis, Cystitis, Dermatitis, Glomerulonephritis, Inflammatory Bowel Disease, Inflammatory Myopathy (e.g., Polymyositis, Dermatomyositis, or Inclusion-body Myositis), Inflammatory Lung Disease, Interstitial Cystitis, Meningitis, Pelvic Inflammatory Disease, Phlebitis, Psoriasis, Reperfusion Injury, Rheumatoid Arthritis, Sarcoidosis, Tendonitis, Tonsilitis, Transplant Rejection, and Vasculitis. In some embodiments, the inflammatory disease or disorder is asthma. |

It should be appreciated that oligonucleotides provided herein for increasing gene expression may be single stranded or double stranded. Single stranded oligonucleotides may include secondary structures, e.g., a loop or helix structure, and thus may have one or more double stranded portions under certain physiochemical conditions. In some embodiments, the oligonucleotide comprises at least one modified nucleotide or modified internucleoside linkage as described herein.

Oligonucleotides provided herein may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches may have increased non-specific binding and/or off-target effects, compared with oligonucleotides that do not have guanosine nucleotide stretches.

Oligonucleotides provided herein may have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than a euchromatic region of a target gene. The threshold level of sequence identity may be 50%, 60%, 70%, 80%, 85%, 90%, 95%, 99% or 100% sequence identity.

Oligonucleotides provided herein may have a sequence that is has greater than 30% G-C content, greater than 40% G-C content, greater than 50% G-C content, greater than 60% G-C content, greater than 70% G-C content, or greater than 80% G-C content. The oligonucleotide may have a sequence that has up to 100% G-C content, up to 95% G-C content, up to 90% G-C content, or up to 80% G-C content. In some embodiments in which the oligonucleotide is 8 to 10 nucleotides in length, all but 1, 2, 3, 4, or 5 of the nucleotides are cytosine or guanosine nucleotides. In some embodiments, the sequence of the mRNA to which the oligonucleotide is complementary comprises no more than 3 nucleotides selected from adenine and uracil.

Oligonucleotides provided herein may be complementary to a target gene of multiple different species (e.g., human, mouse, rat, rabbit, goat, monkey, etc.). Oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease.

In some embodiments, the region of complementarity of an oligonucleotide is complementary with at least 5 to 15, 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of target gene (e.g., within a euchromatic region of a target gene). In some embodiments, the region of complementarity is complementary with at least 5 or at least 8 consecutive nucleotides of target gene (e.g., within a euchromatic region of a target gene). In some embodiments, oligonucleotide comprises a region of complementarity that hybridizes with an RNA transcript or DNA strand, or a portion of either one, said portion having a length of about 5 to 40, or about 8 to 40, or about 5 to 15, or about 5 to 30, or about 5 to 40, or about 5 to 50 contiguous nucleotides.

Complementary, as the term is used in the art, refers to the capacity for precise pairing between two nucleotides. For example, if a nucleotide at a certain position of an oligonucleotide is capable of hydrogen bonding with a nucleotide at the same position of a target nucleic acid (e.g., an RNA transcript, DNA strand), then the oligonucleotide and the target nucleic acid are considered to be complementary to each other at that position. The oligonucleotide and the target nucleic acid are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the oligonucleotide and its target nucleic acid. For example, if a base at one position of an oligonucleotide is capable of hydrogen bonding with a base at the corresponding position of a target nucleic acid, then the bases are considered to be complementary to each other at that position. 100% complementarity is not required.

The oligonucleotide may be at least 80% complementary to (optionally one of at least 85%, 90%, 91%, 92%, 93%, 94%, 95%, 96%, 97%, 98%, 99% or 100% complementary to) the consecutive nucleotides of a target nucleic acid. In some embodiments the oligonucleotide may contain 1, 2 or 3 base mismatches compared to the portion of the consecutive nucleotides of a target nucleic acid. In some embodiments the oligonucleotide may have up to 3 mismatches over 15 bases, or up to 2 mismatches over 10 bases.

It is understood in the art that a complementary nucleotide sequence need not be 100% complementary to that of its target nucleic acid to be specifically hybridizable or specific for a target nucleic acid. In some embodiments, a complementary nucleic acid sequence for purposes of the present disclosure is specifically hybridizable or specific for the target nucleic when binding of the sequence to the target nucleic acid (e.g., RNA transcript, DNA strand) results in increased expression of a target gene and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency.

In some embodiments, the oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length. In a preferred embodiment, the oligonucleotide is 8 to 30 nucleotides in length.

Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa.

In some embodiments, GC content of the oligonucleotide is preferably between about 30-60%. Contiguous runs of three or more Gs or Cs may not be preferable in some embodiments. Accordingly, in some embodiments, the oligonucleotide does not comprise a stretch of three or more guanosine nucleotides.

It is to be understood that any oligonucleotide provided herein can be excluded.

In some embodiments, an oligonucleotide is not complementary to a natural antisense transcript as disclosed in PCT Publication No. WO12170771. In some embodiments, the oligonucleotide is not complementary to the nucleotide sequence of SEQ ID NO: 2 as disclosed in PCT Publication No. WO12170771A1.

In some embodiments, an oligonucleotide is not complementary to a natural antisense transcript as disclosed in US Patent Publication No. US2011294870. In some embodiments, the oligonucleotide is not complementary to the nucleotide sequence of any of SEQ ID NOs: 4, 5, 6, 6a, 6b, 7, 8, 9, 10, 14 or 15 as disclosed in US Patent Publication No. US2011294870.

In some embodiments, an oligonucleotide is not complementary to a natural antisense transcript as disclosed in US Patent Publication No. US2010280100. In some embodiments, the oligonucleotide is not complementary to the nucleotide sequence of SEQ ID NO: 3 as disclosed in US Patent Publication No. US2010280100.

In some embodiments, an oligonucleotide is not complementary to a natural antisense transcript as disclosed in US Patent Publication No. US2010105760. In some embodiments, the oligonucleotide is not complementary to the nucleotide sequence of any of SEQ ID NOs: 2, 175, or 176 as disclosed in US Patent Publication No. US2010105760.

In some embodiments, an oligonucleotide is not complementary to a natural antisense transcript as disclosed in US Patent Publication No. US2011319475. In some embodiments, the oligonucleotide is not complementary to the nucleotide sequence of SEQ ID NO: 2 as disclosed in US Patent Publication No. US2011319475.

In some embodiments, an oligonucleotide is not complementary to a natural antisense transcript as disclosed in US Patent Publication No. US2012129917. In some embodiments, the oligonucleotide is not complementary to the nucleotide sequence of any of SEQ ID NOs: 3, 4, 5, or 6 as disclosed in US Patent Publication No. US2012129917.

In some embodiments, an oligonucleotide is not complementary to a natural antisense transcript as disclosed in US Patent Publication No. US2012046344. In some embodiments, the oligonucleotide is not complementary to the nucleotide sequence of any of SEQ ID NOs: 8 to 22 as disclosed in US Patent Publication No. US2012046344.

In some embodiments, an oligonucleotide is not complementary to a natural antisense transcript as disclosed in PCT Publication No. WO12068340. In some embodiments, the oligonucleotide is not complementary to the nucleotide sequence of any of SEQ ID NOs: 9 to 13 or FIG. 1 as disclosed in PCT Publication No. WO12068340.

In some embodiments, an oligonucleotide is not complementary to a natural antisense transcript as disclosed in US Patent Publication No. US2012046345. In some embodiments, the oligonucleotide is not complementary to the nucleotide sequence of any of SEQ ID NOs: 3 to 7 as disclosed in US Patent Publication No. US2012046345.

In some embodiments, an oligonucleotide is not complementary to a natural antisense transcript as disclosed in PCT Publication No. WO12068340. In some embodiments, the oligonucleotide is not complementary to the nucleotide sequence of any of SEQ ID NOs: 9 to 13 or FIG. 1 as disclosed in PCT Publication No. WO12068340.

In some embodiments, an oligonucleotide is not complementary to a natural antisense transcript as disclosed in US Patent Publication No. US2011237649. In some embodiments, the oligonucleotide is not complementary to the nucleotide sequence of any of SEQ ID NOs: 3 to 6 as disclosed in US Patent Publication No. US2011237649.

In some embodiments, an oligonucleotide is not complementary to a natural antisense transcript as disclosed in US Patent Publication No. US2011319317. In some embodiments, the oligonucleotide is not complementary to the nucleotide sequence of any of SEQ ID NOs: 3 to 8 as disclosed in US Patent Publication No. US2011319317.

In some embodiments, an oligonucleotide is not complementary to a natural antisense transcript as disclosed in US Patent Publication No. US2012252869. In some embodiments, the oligonucleotide is not complementary to the nucleotide sequence of any of SEQ ID NOs: 5 to 14 as disclosed in US Patent Publication No. US2012252869.

In some embodiments, an oligonucleotide is not complementary to a natural antisense transcript as disclosed in US Patent Publication No. US2013072421. In some embodiments, the oligonucleotide is not complementary to the nucleotide sequence of any of SEQ ID NOs: 9 to 23 or 141 to 143 as disclosed in US Patent Publication No. US2013072421.

In some embodiments, an oligonucleotide is not complementary to a natural antisense transcript as disclosed in PCT Publication No. WO11146674. In some embodiments, the oligonucleotide is not complementary to the nucleotide sequence of any of SEQ ID NOs: 2 or 3 as disclosed in PCT Publication No. WO11146674.

In some embodiments, an oligonucleotide is not complementary to a natural antisense transcript as disclosed in US Patent Publication No. US2012064048. In some embodiments, the oligonucleotide is not complementary to the nucleotide sequence of any of SEQ ID NOs: 4 to 6 as disclosed in US Patent Publication No. US2012064048.

In some embodiments, an oligonucleotide is not complementary to a natural antisense transcript as disclosed in PCT Publication No. WO12071238. In some embodiments, the oligonucleotide is not complementary to the nucleotide sequence of SEQ ID NO: 2 as disclosed in PCT Publication No. WO12071238.

In some embodiments, an oligonucleotide is not complementary to a natural antisense transcript as disclosed in US Patent Publication No. US2011237651. In some embodiments, the oligonucleotide is not complementary to the nucleotide sequence of any of SEQ ID NOs: 2 or 3 as disclosed in US Patent Publication No. US2011237651.

In some embodiments, an oligonucleotide is not complementary to a natural antisense transcript as disclosed in PCT Publication No. WO11139387. In some embodiments, the oligonucleotide is not complementary to the nucleotide sequence of any of SEQ ID NOs: 9 to 23, 142, or 143 as disclosed in PCT Publication No. WO11139387.

In some embodiments, an oligonucleotide is not complementary to a natural antisense transcript as disclosed in US Patent Publication No. US2011237650. In some embodiments, the oligonucleotide is not complementary to the nucleotide sequence of any of SEQ ID NOs: 2 or 3 as disclosed in US Patent Publication No. US2011237650.

In some embodiments, an oligonucleotide is not complementary to a natural antisense transcript as disclosed in US Patent Publication No. US2012149759. In some embodiments, the oligonucleotide is not complementary to the nucleotide sequence of any of SEQ ID NOs: 2 or 3 as disclosed in US Patent Publication No. US2012149759.

In some embodiments, an oligonucleotide is not complementary to a natural antisense transcript as disclosed in US Patent Publication No. US2012329855. In some embodiments, the oligonucleotide is not complementary to the nucleotide sequence of any of SEQ ID NOs: 2 to 4 as disclosed in US Patent Publication No. US2012329855.

In some embodiments, an oligonucleotide is not complementary to a natural antisense transcript as disclosed in US Patent Publication No. US2013035372. In some embodiments, the oligonucleotide is not complementary to the nucleotide sequence of SEQ ID NO: 2 as disclosed in US Patent Publication No. US2013035372.

In some embodiments, an oligonucleotide is not complementary to a natural antisense transcript as disclosed in US Patent Publication No. US2012309814. In some embodiments, the oligonucleotide is not complementary to the nucleotide sequence of SEQ ID NO: 2 as disclosed in US Patent Publication No. US2012309814.

In some embodiments, an oligonucleotide is not complementary to a natural antisense transcript as disclosed in US Patent Publication No. US2013035373. In some embodiments, the oligonucleotide is not complementary to the nucleotide sequence of SEQ ID NO: 2 as disclosed in US Patent Publication No. US2013035373.

In some embodiments, an oligonucleotide is not complementary to a natural antisense transcript as disclosed in US Patent Publication No. US2012329727. In some embodiments, the oligonucleotide is not complementary to the nucleotide sequence of any of SEQ ID NOs: 2 or 3 as disclosed in US Patent Publication No. US2012329727.

In some embodiments, an oligonucleotide is not complementary to a natural antisense transcript as disclosed in US Patent Publication No. US2012322853. In some embodiments, the oligonucleotide is not complementary to the nucleotide sequence of any of SEQ ID NOs: 6 to 12 as disclosed in US Patent Publication No. US2012322853.

In some embodiments, an oligonucleotide is not complementary to a natural antisense transcript as disclosed in US Patent Publication No. US2012088817. In some embodiments, the oligonucleotide is not complementary to the nucleotide sequence of any of SEQ ID NOs: 4 to 9 as disclosed in US Patent Publication No. US2012088817.

In some embodiments, an oligonucleotide is not complementary to a natural antisense transcript as disclosed in US Patent Publication No. US2012094934. In some embodiments, the oligonucleotide is not complementary to the nucleotide sequence of any of SEQ ID NOs: 2 or 3 as disclosed in US Patent Publication No. US2012094934.

In some embodiments, an oligonucleotide is not complementary to a natural antisense transcript as disclosed in US Patent Publication No. US2012142758. In some embodiments, the oligonucleotide is not complementary to the nucleotide sequence of any of SEQ ID NOs: 3 to 6 as disclosed in US Patent Publication No. US2012142758.

In some embodiments, an oligonucleotide is not complementary to a natural antisense transcript as disclosed in US Patent Publication No. US2012095081. In some embodiments, the oligonucleotide is not complementary to the nucleotide sequence of SEQ ID NO: 2 as disclosed in US Patent Publication No. US2012095081.

In some embodiments, an oligonucleotide is not complementary to a natural antisense transcript as disclosed in US Patent Publication No. US2012171170. In some embodiments, the oligonucleotide is not complementary to the nucleotide sequence of any of SEQ ID NOs: 4 to 9 as disclosed in US Patent Publication No. US2012171170.

In some embodiments, an oligonucleotide is not complementary to a natural antisense transcript as disclosed in US Patent Publication No. US2012046236. In some embodiments, the oligonucleotide is not complementary to the nucleotide sequence of any of SEQ ID NOs: 3 to 5 as disclosed in US Patent Publication No. US2012046236.

In some embodiments, an oligonucleotide is not complementary to a natural antisense transcript as disclosed in US Patent Publication No. US2012277290. In some embodiments, the oligonucleotide is not complementary to the nucleotide sequence of any of SEQ ID NOs: 2 or 3 as disclosed in US Patent Publication No. US2012277290.

In some embodiments, an oligonucleotide is not complementary to a natural antisense transcript as disclosed in US Patent Publication No. US2012289583. In some embodiments, the oligonucleotide is not complementary to the nucleotide sequence of any of SEQ ID NOs: 2 or 3 as disclosed in US Patent Publication No. US2012289583.

In some embodiments, an oligonucleotide is not complementary to a natural antisense transcript as disclosed in US Patent Publication No. US2012095079. In some embodiments, the oligonucleotide is not complementary to the nucleotide sequence of SEQ ID NO: 3 as disclosed in US Patent Publication No. US2012095079.

In some embodiments, an oligonucleotide is not complementary to a natural antisense transcript as disclosed in US Patent Publication No. US2013096183. In some embodiments, the oligonucleotide is not complementary to the nucleotide sequence of any of SEQ ID NOs: 12 to 28 as disclosed in US Patent Publication No. US2013096183.

In some embodiments, an oligonucleotide is not complementary to a natural antisense transcript as disclosed in US Patent Publication No. US2013116300. In some embodiments, the oligonucleotide is not complementary to the nucleotide sequence of SEQ ID NO: 2 as disclosed in US Patent Publication No. US2013116300.

In some embodiments, an oligonucleotide is not complementary to a natural antisense transcript as disclosed in US Patent Publication No. US2012010156. In some embodiments, the oligonucleotide is not complementary to the nucleotide sequence of SEQ ID NO: 3 as disclosed in US Patent Publication No. US2012010156.

In some embodiments, an oligonucleotide is not complementary to a natural antisense transcript as disclosed in US Patent Publication No. US2012004184. In some embodiments, the oligonucleotide is not complementary to the nucleotide sequence of SEQ ID NO: 3 as disclosed in US Patent Publication No. US2012004184.

In some embodiments, an oligonucleotide is not complementary to a natural antisense transcript as disclosed in US Patent Publication No. US2013065947. In some embodiments, the oligonucleotide is not complementary to the nucleotide sequence of SEQ ID NO: 2 as disclosed in US Patent Publication No. US2013065947.

In some embodiments, an oligonucleotide is not complementary to a natural antisense transcript as disclosed in US Patent Publication No. US2013085112. In some embodiments, the oligonucleotide is not complementary to the nucleotide sequence of SEQ ID NO: 2 as disclosed in US Patent Publication No. US2013085112.

In some embodiments, an oligonucleotide is not complementary to a natural antisense transcript as disclosed in US Patent Publication No. US2013085112. In some embodiments, the oligonucleotide is not complementary to the nucleotide sequence of SEQ ID NO: 2 as disclosed in US Patent Publication No. US2013085112.

In some embodiments, an oligonucleotide is not complementary to a natural antisense transcript as disclosed in US Patent Publication No. US2013137751. In some embodiments, the oligonucleotide is not complementary to the nucleotide sequence of any of SEQ ID NOs: 2 to 4 or 42 to 44 as disclosed in US Patent Publication No. US2013137751.

In some embodiments, an oligonucleotide is not complementary to a natural antisense transcript as disclosed in US Patent Publication No. US2011319476. In some embodiments, the oligonucleotide is not complementary to the nucleotide sequence of any of SEQ ID NOs: 2 to 4 or 42 to 44 as disclosed in US Patent Publication No. US2011319476.

In some embodiments, an oligonucleotide is not complementary to a natural antisense transcript as disclosed in PCT Publication No. WO11146675. In some embodiments, the oligonucleotide is not complementary to the nucleotide sequence of any of SEQ ID NOs: 2 to 4 as disclosed in PCT Publication No. WO11146675.

In some embodiments, an oligonucleotide is not complementary to a natural antisense transcript as disclosed in US Patent Publication No. US2013072546. In some embodiments, the oligonucleotide is not complementary to the nucleotide sequence of SEQ ID NO: 2 as disclosed in US Patent Publication No. US2013072546.

In some embodiments, an oligonucleotide is not complementary to a natural antisense transcript as disclosed in US Patent Publication No. US2013143946. In some embodiments, the oligonucleotide is not complementary to the nucleotide sequence of SEQ ID NO: 2 as disclosed in US Patent Publication No. US2013143946.

In some embodiments, an oligonucleotide is not complementary to a natural antisense transcript as disclosed in PCT Publication No. WO12054723. In some embodiments, the oligonucleotide is not complementary to the nucleotide sequence of any of SEQ ID NOs: 2 to 9 as disclosed in PCT Publication No. WO12054723.

In some embodiments, an oligonucleotide is not complementary to a natural antisense transcript as disclosed in PCT Publication No. WO12058268. In some embodiments, the oligonucleotide is not complementary to the nucleotide sequence of any of SEQ ID NOs: 2 to 7 as disclosed in PCT Publication No. WO12058268.

In some embodiments, an oligonucleotide is not complementary to a natural antisense transcript as disclosed in US Patent Publication No. US2012142610. In some embodiments, the oligonucleotide is not complementary to the nucleotide sequence of SEQ ID NO: 2 as disclosed in US Patent Publication No. US2012142610.

In some embodiments, an oligonucleotide is not complementary to a natural antisense transcript as disclosed in US Patent Publication No. US2012135941. In some embodiments, the oligonucleotide is not complementary to the nucleotide sequence of any of SEQ ID NOs: 2 or 3 as disclosed in US Patent Publication No. US2012135941.

In some embodiments, an oligonucleotide is not complementary to a natural antisense transcript as disclosed in PCT Publication No. WO12047956. In some embodiments, the oligonucleotide is not complementary to the nucleotide sequence of any of SEQ ID NOs: 2 to 7 as disclosed in PCT Publication No. WO12047956.

In some embodiments, an oligonucleotide is not complementary to a natural antisense transcript as disclosed in PCT Publication No. WO12024478. In some embodiments, the oligonucleotide is not complementary to the nucleotide sequence of any of SEQ ID NOs: 2 to 16 as disclosed in PCT Publication No. WO12024478.

In some embodiments, an oligonucleotide is not complementary to a natural antisense transcript as disclosed in PCT Publication No. WO12009347. In some embodiments, the oligonucleotide is not complementary to the nucleotide sequence of SEQ ID NO: 2 as disclosed in PCT Publication No. WO12009347.

In some embodiments, an oligonucleotide is not complementary to a natural antisense transcript as disclosed in PCT Publication No. WO11097582. In some embodiments, the oligonucleotide is not complementary to the nucleotide sequence of SEQ ID NO: 2 as disclosed in PCT Publication No. WO11097582.

In some embodiments, an oligonucleotide is not complementary to a natural antisense transcript as disclosed in PCT Publication No. WO11038205. In some embodiments, the oligonucleotide is not complementary to the nucleotide sequence of SEQ ID NO: 2 as disclosed in PCT Publication No. WO11038205.

In some embodiments, an oligonucleotide is not complementary to a natural antisense transcript as disclosed in PCT Publication No. WO11025862. In some embodiments, the oligonucleotide is not complementary to the nucleotide sequence of any of SEQ ID NOs: 2 or 3 as disclosed in PCT Publication No. WO11025862.

In some embodiments, an oligonucleotide is not complementary to a natural antisense transcript as disclosed in US Patent Publication No. US2012295959. In some embodiments, the oligonucleotide is not complementary to the nucleotide sequence of any of SEQ ID NOs: 2 to 5 as disclosed in US Patent Publication No. US2012295959.

In some embodiments, an oligonucleotide is not complementary to a natural antisense transcript as disclosed in US Patent Publication No. US2012295952. In some embodiments, the oligonucleotide is not complementary to the nucleotide sequence of SEQ ID NO: 2 as disclosed in US Patent Publication No. US2012295952.

In some embodiments, an oligonucleotide is not complementary to a natural antisense transcript as disclosed in US Patent Publication No. US2012295954. In some embodiments, the oligonucleotide is not complementary to the nucleotide sequence of SEQ ID NO: 2 as disclosed in US Patent Publication No. US2012295954.

In some embodiments, an oligonucleotide is not complementary to a natural antisense transcript as disclosed in US Patent Publication No. US2012295953. In some embodiments, the oligonucleotide is not complementary to the nucleotide sequence of SEQ ID NO: 2 as disclosed in US Patent Publication No. US2012295953.

In some embodiments, an oligonucleotide is not complementary to a natural antisense transcript as disclosed in US Patent Publication No. US2012264812. In some embodiments, the oligonucleotide is not complementary to the nucleotide sequence of SEQ ID NO: 2 as disclosed in US Patent Publication No. US2012264812.

In some embodiments, an oligonucleotide is not complementary to a natural antisense transcript as disclosed in PCT Publication No. WO13036403.

In some embodiments, it has been found that oligonucleotides disclosed herein may increase expression of a target gene by at least about 50% (i.e. 150% of normal or 1.5 fold), or by about 2 fold to about 5 fold. In some embodiments, expression may be increased by at least about 15 fold, 20 fold, 30 fold, 40 fold, 50 fold or 100 fold, or any range between any of the foregoing numbers.

The oligonucleotides described herein may be modified, e.g., comprise a modified sugar moiety, a modified internucleoside linkage, a modified nucleotide and/or combinations thereof. In addition, the oligonucleotides may exhibit one or more of the following properties: do not mediate alternative splicing; are not immune stimulatory; are nuclease resistant; have improved cell uptake compared to unmodified oligonucleotides; are not toxic to cells or mammals; or have improved endosomal exit.

Any of the oligonucleotides disclosed herein may be linked to one or more other oligonucleotides disclosed herein by a linker, e.g., a cleavable linker.

Oligonucleotides of the invention can be stabilized against nucleolytic degradation such as by the incorporation of a modification, e.g., a nucleotide modification. For example, nucleic acid sequences of the invention include a phosphorothioate at least the first, second, or third internucleoside linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

Any of the modified chemistries or formats of oligonucleotides described herein can be combined with each other, and that one, two, three, four, five, or more different types of modifications can be included within the same molecule.

In some embodiments, an oligonucleotide may comprise one or more modified nucleotides (also referred to herein as nucleotide analogs). In some embodiments, the oligonucleotide may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States Patent or Patent Application Publications: U.S. Pat. No. 7,399,845, U.S. Pat. No. 7,741,457, U.S. Pat. No. 8,022,193, U.S. Pat. No. 7,569,686, U.S. Pat. No. 7,335,765, U.S. Pat. No. 7,314,923, U.S. Pat. No. 7,335,765, and U.S. Pat. No. 7,816,333, US 20110009471, the entire contents of each of which are incorporated herein by reference for all purposes. The oligonucleotide may have one or more 2' O-methyl nucleotides. The oligonucleotide may consist entirely of 2' O-methyl nucleotides.

Often the oligonucleotide has one or more nucleotide analogues. For example, the oligonucleotide may have at least one nucleotide analogue that results in an increase in $T_m$ of the oligonucleotide in a range of 1° C., 2° C., 3° C., 4° C., or 5° C. compared with an oligonucleotide that does not have the at least one nucleotide analogue. The oligonucleotide may have a plurality of nucleotide analogues that results in a total increase in $T_m$ of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

The oligonucleotide may be of up to 50 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are nucleotide analogues. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are nucleotide analogues. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are nucleotide analogues. Optionally, the oligonucleotides may have every nucleotide except 1, 2, 3, 4, 5, 6, 7, 8, 9, or 10 nucleotides modified.

The oligonucleotide may consist entirely of bridged nucleotides (e.g., LNA nucleotides, cEt nucleotides, ENA nucleotides). The oligonucleotide may comprise alternating deoxyribonucleotides and 2'-fluoro-deoxyribonucleotides. The oligonucleotide may comprise alternating deoxyribonucleotides and 2'-O-methyl nucleotides. The oligonucleotide may comprise alternating deoxyribonucleotides and ENA nucleotide analogues. The oligonucleotide may comprise alternating deoxyribonucleotides and LNA nucleotides. The oligonucleotide may comprise alternating LNA nucleotides and 2'-O-methyl nucleotides. The oligonucleotide may have a 5' nucleotide that is a bridged nucleotide (e.g., a LNA nucleotide, cEt nucleotide, ENA nucleotide). The oligonucleotide may have a 5' nucleotide that is a deoxyribonucleotide.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide may have a 3' hydroxyl group. The 3' position of the oligonucleotide may have a 3' thiophosphate.

The oligonucleotide may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

Preferably the oligonucleotide comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the oligonucleotide comprises at least one nucleotide modified at the 2' position of the sugar, preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. In some embodiments, oligonucleotides may have phosphorothioate backbones; heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula.

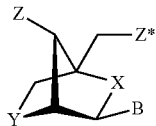

where X and Y are independently selected among the groups —O—,
—S—, —N(H)—, N(R)—, —CH$_2$— or —CH— (if part of a double bond),
—CH$_2$—O—, —CH$_2$—S—, —CH$_2$—N(H)—, —CH$_2$—N(R)—, —CH$_2$—CH$_2$— or —CH$_2$—CH— (if part of a double bond),
—CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

In some embodiments, the LNA used in the oligonucleotides described herein comprises at least one LNA unit according any of the formulas

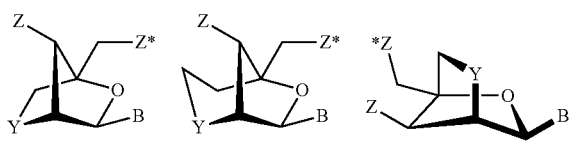

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

In some embodiments, the Locked Nucleic Acid (LNA) used in the oligonucleotides described herein comprises at least one Locked Nucleic Acid (LNA) unit according any of the formulas shown in Scheme 2 of PCT/DK2006/000512.

In some embodiments, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically preferred LNA units are shown below:

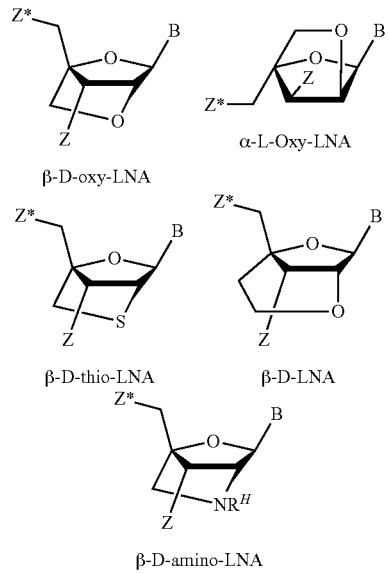

β-D-oxy-LNA    α-L-Oxy-LNA

β-D-thio-LNA    β-D-LNA

β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail herein.

One or more substituted sugar moieties can also be included, e.g., one of the following at the 2' position: OH, SH, SCH$_3$, F, OCN, OCH$_3$OCH$_3$, OCH$_3$O(CH$_2$)n CH$_3$, O(CH$_2$)n NH$_2$ or O(CH$_2$)n CH$_3$ where n is from 1 to about 10; C1 to C10 lower alkyl, alkoxyalkoxy, substituted lower alkyl, alkaryl or aralkyl; Cl; Br; CN; CF$_3$; OCF$_3$; O—, S—, or N-alkyl; O-, S-, or N-alkenyl; SOCH$_3$; SO$_2$CH$_3$; ONO$_2$; NO$_2$; N$_3$; NH2; heterocycloalkyl; heterocycloalkaryl; amino alkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy[2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O—CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Oligonucleotides can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the oligonucleotides are chemically linked to one or more moieties or conjugates that enhance the activity, cellular distribution, or cellular uptake of the oligonucleotide. For example, one or more oligonucleotides, of the same or different types, can be conjugated to each other; or oligonucleotides can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, oligonucleotide modification includes modification of the 5' or 3' end of the oligonucleotide. In some embodiments, the 3' end of the oligonucleotide comprises a hydroxyl group or a thiophosphate. It should be appreciated that additional molecules (e.g. a biotin moiety or a fluorophor) can be conjugated to the 5' or 3' end of the oligonucleotide. In some embodiments, the oligonucleotide comprises a biotin moiety conjugated to the 5' nucleotide.

In some embodiments, the oligonucleotide comprises locked nucleic acids (LNA), ENA modified nucleotides, 2'-O-methyl nucleotides, or 2'-fluoro-deoxyribonucleotides. In some embodiments, the oligonucleotide comprises alternating deoxyribonucleotides and 2'-fluoro-deoxyribonucleotides. In some embodiments, the oligonucleotide comprises alternating deoxyribonucleotides and 2'-O-methyl nucleotides. In some embodiments, the oligonucleotide comprises alternating deoxyribonucleotides and ENA modified nucleotides. In some embodiments, the oligonucleotide comprises alternating deoxyribonucleotides and locked nucleic acid nucleotides. In some embodiments, the oligonucleotide comprises alternating locked nucleic acid nucleotides and 2'-O-methyl nucleotides.

In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the oligonucleotide comprises phosphorothioate internucleoside linkages. In some embodiments, the oligonucleotide comprises phosphorothioate internucleoside linkages between at least two nucleotides. In some embodiments, the oligonucleotide comprises phosphorothioate internucleoside linkages between all nucleotides.

It should be appreciated that the oligonucleotide can have any combination of modifications as described herein.

In some embodiments, an oligonucleotide described herein may be a mixmer or comprise a mixmer sequence pattern. The term 'mixmer' refers to oligonucleotides which comprise both naturally and non-naturally occurring nucleotides or comprise two different types of non-naturally occurring nucleotides. Mixmers are generally known in the art to have a higher binding affinity than unmodified oligonucleotides and may be used to specifically bind a target molecule, e.g., to block a binding site on the target molecule. Generally, mixmers do not recruit an RNAse to the target molecule and thus do not promote cleavage of the target molecule.

In some embodiments, the mixmer comprises or consists of a repeating pattern of nucleotide analogues and naturally occurring nucleotides, or one type of nucleotide analogue and a second type of nucleotide analogue. However, it is to be understood that the mixmer need not comprise a repeating pattern and may instead comprise any arrangement of nucleotide analogues and naturally occurring nucleotides or any arrangement of one type of nucleotide analogue and a second type of nucleotide analogue. The repeating pattern, may, for instance be every second or every third nucleotide is a nucleotide analogue, such as LNA, and the remaining nucleotides are naturally occurring nucleotides, such as DNA, or are a 2' substituted nucleotide analogue such as 2'MOE or 2' fluoro analogues, or any other nucleotide analogues described herein. It is recognised that the repeating pattern of nucleotide analogues, such as LNA units, may be combined with nucleotide analogues at fixed positions—e.g. at the 5' or 3' termini.

In some embodiments, the mixmer does not comprise a region of more than 5, more than 4, more than 3, or more than 2 consecutive naturally occurring nucleotides, such as DNA nucleotides. In some embodiments, the mixmer comprises at least a region consisting of at least two consecutive nucleotide analogues, such as at least two consecutive LNAs. In some embodiments, the mixmer comprises at least a region consisting of at least three consecutive nucleotide analogue units, such as at least three consecutive LNAs.

In some embodiments, the mixmer does not comprise a region of more than 7, more than 6, more than 5, more than 4, more than 3, or more than 2 consecutive nucleotide analogues, such as LNAs. It is to be understood that the LNA units may be replaced with other nucleotide analogues, such as those referred to herein.

In some embodiments, the mixmer comprises at least one nucleotide analogue in one or more of six consecutive nucleotides. The substitution pattern for the nucleotides may be selected from the group consisting of Xxxxxx, xXxxxx, xxXxxx, xxxXxx, xxxxXx and xxxxxX, wherein "X" denotes a nucleotide analogue, such as an LNA, and "x" denotes a naturally occurring nucleotide, such as DNA or RNA.

In some embodiments, the mixmer comprises at least two nucleotide analogues in one or more of six consecutive nucleotides. The substitution pattern for the nucleotides may be selected from the group consisting of XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX and xxxxXX, wherein "X" denotes a nucleotide analogue, such as an LNA, and "x" denotes a naturally occurring nucleotide, such as DNA or RNA. In some embodiments, the substitution pattern for the nucleotides may be selected from the group consisting of XxXxxx, XxxXxx, XxxxXx, XxxxxX, xXxXxx, xXxxXx, xXxxxX, xxXxXx, xxXxxX and xxxXxX. In some embodiments, the substitution pattern is selected from the group consisting of xXxXxx, xXxxXx, xXxxxX, xxXxXx, xxXxxX and xxxXxX. In some embodiments, the substitution pattern is selected from the group consisting of xXxXxx, xXxxXx and xxXxXx. In some embodiments, the substitution pattern for the nucleotides is xXxXxx.

In some embodiments, the mixmer comprises at least three nucleotide analogues in one or more of six consecutive nucleotides. The substitution pattern for the nucleotides may be selected from the group consisting of XXXxxx, xXXXxx, xxXXXx, xxxXXX, XXxXxx, XXxxXx, XXxxxX, xXXxXx, xXXxxX, xxXXxX, XxXXxx, XxxXXx, XxxxXX, XxXxXx, XxXxxX, XxxXxX, XxxXxX, XxxxXX, xXxXxX, xXxxXX, xxXxXX, xXxXxX and XxXxXx, wherein "X" denotes a nucleotide analogue, such as an LNA, and "x" denotes a naturally occurring nucleotide, such as DNA or RNA. In some embodiments, the substitution pattern for the nucleotides is selected from the group consisting of XXxXxx, XXxxXx, XXxxxX, xXXxXx, xXXxxX, xxXXxX, XxXXxx, XxxXXx, XxxxXX, XxXxXx, XxXxxX, XxxXxX, xXxXxX, xXxxXX, xxXxXX, xXxXxX and XxXxXx. In some embodiments, the substitution pattern for the nucleotides is selected from the group consisting of xXXxXx, xXXxxX, xxXXxX, xXxXXx, xXxxXX, xxXxXX and xXxXxX. In some embodiments, the substitution pattern for the nucleotides is xXxXxX or XxXxXx. In some embodiments, the substitution pattern for the nucleotides is xXxXxX.

In some embodiments, the mixmer comprises at least four nucleotide analogues in one or more of six consecutive nucleotides. The substitution pattern for the nucleotides may be selected from the group consisting of xXXXX, xXxXXX, xXXxXX, xXXXxX, xXXXXx, XxxXXX, XxXxXX, XxXXxX, XxXXXx, XxXxXx, XXxxXX, XXxXxX, XXxXXx, XXXxxX, XXXxXx, XXXXxx and XXXXxx, wherein "X" denotes a nucleotide analogue, such as an LNA, and "x" denotes a naturally occurring nucleotide, such as DNA or RNA.

In some embodiments, the mixmer comprises at least five nucleotide analogues in one or more of six consecutive nucleotides. The substitution pattern for the nucleotides may be selected from the group consisting of xXXXXX, XxXXXX, XXxXXX, XXXxXX, XXXXxX and XXXXXx, wherein "X" denotes a nucleotide analogue, such as an LNA, and "x" denotes a naturally occurring nucleotide, such as DNA or RNA.

The oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)xXxXXx, (X)xXxxXX, (X)xxXxXX, (X)xXxXxX and (X)XxXxXx, (d) (X)xxXXXX, (X)xXxXXX, (X)xXXxXX, (X)xXXXxX, (X)xXXXXx, (X)XxxXXX, (X)XxXxXX, (X)XxXXxX, (X)XxXXXx, (X)XxXxXx, (X)XXxxXX, (X)XXxXxX, (X)XXxXXx, (X)XXXxxX, (X)XXXxXx, (X)XXXXxx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

In some embodiments, the mixmer contains a modified nucleotide, e.g., an LNA, at the 5' end. In some embodiments, the mixmer contains a modified nucleotide, e.g., an LNA, at the first two positions, counting from the 5' end.

In some embodiments, the mixmer is incapable of recruiting RNAseH. Oligonucleotides that are incapable of recruiting RNAseH are well known in the literature, in example see WO2007/112754, WO2007/112753, or PCT/DK2008/000344. Mixmers may be designed to comprise a mixture of affinity enhancing nucleotide analogues, such as in non-limiting example LNA nucleotides and 2'-O-methyl nucleotides. In some embodiments, the mixmer comprises modified internucleoside linkages (e.g., phosphorothioate internucleoside linkages or other linkages) between at least two, at least three, at least four, at least five or more nucleotides.

A mixmer may be produced using any method known in the art or described herein. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

In some embodiments, the oligonucleotide is a gapmer. A gapmer oligonucleotide generally has the formula 5'-X—Y—Z-3', with X and Z as flanking regions around a gap region Y. In some embodiments, the Y region is a contiguous stretch of nucleotides, e.g., a region of at least 6 DNA nucleotides, which are capable of recruiting an RNAse, such as RNAseH. Without wishing to be bound by theory, it is thought that the gapmer binds to the target nucleic acid, at which point an RNAse is recruited and can then cleave the target nucleic acid. In some embodiments, the Y region is flanked both 5' and 3' by regions X and Z comprising high-affinity modified nucleotides, e.g., 1-6 modified nucleotides. Exemplary modified oligonucleotides include, but are not limited to, 2' MOE or 2'OMe or Locked Nucleic Acid bases (LNA). The flanks X and Z may be have a of a length 1-20 nucleotides, preferably 1-8 nucleotides and even more preferred 1-5 nucleotides. The flanks X and Z may be of similar length or of dissimilar lengths. The gap-segment Y may be a nucleotide sequence of length 5-20 nucleotides, preferably 6-12 nucleotides and even more preferred 6-10 nucleotides. In some aspects, the gap region of the gapmer oligonucleotides of the invention may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleosides. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using any method known in the art or described herein. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,432,250; and 7,683,036; U.S. patent publication Nos. US20090286969, US20100197762, and US20110112170; and PCT publication Nos. WO2008049085 and WO2009090182, each of which is herein incorporated by reference in its entirety.

In some embodiments, oligonucleotides provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

Following selection of an appropriate target RNA sequence, siRNA molecules that comprise a nucleotide sequence complementary to all or a portion of the target sequence, i.e. an antisense sequence, can be designed and prepared using any method known in the art (see, e.g., PCT Publication Nos. WO08124927A1 and WO 2004/016735; and U.S. Patent Publication Nos. 2004/0077574 and 2008/0081791). A number of commercial packages and services are available that are suitable for use for the preparation of siRNA molecules. These include the in vitro transcription kits available from Ambion (Austin, Tex.) and New England Biolabs (Beverly, Mass.) as described above; viral siRNA construction kits commercially available from Invitrogen (Carlsbad, Calif.) and Ambion (Austin, Tex.), and custom siRNA construction services provided by Ambion (Austin, Tex.), Qiagen (Valencia, Calif.), Dharmacon (Lafayette, Colo.) and Sequitur, Inc (Natick, Mass.). A target sequence can be selected (and a siRNA sequence designed) using computer software available commercially (e.g. OligoEngine™ (Seattle, Wash.); Dharmacon, Inc. (Lafayette, Colo.); Target Finder from Ambion Inc. (Austin, Tex.) and the siRNA Design Tool from QIAGEN, Inc. (Valencia, Calif.)). In some embodiments, an siRNA may be designed or obtained using the RNAi atlas (available at the RNAiAtlas website), the siRNA database (available at the Stockholm Bioinformatics Website), or using DesiRM (available at the Institute of Microbial Technology website).

The siRNA molecule can be double stranded (i.e. a dsRNA molecule comprising an antisense strand and a complementary sense strand) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

Double-stranded siRNA may comprise RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or the 5' end of either or both strands). A spacer sequence is may be an unrelated nucleotide sequence that is situated between two complementary nucleotide sequence regions which, when annealed into a double-stranded nucleic acid, comprise a shRNA.

The overall length of the siRNA molecules can vary from about 14 to about 200 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 200 nucleotides.

An siRNA molecule may comprise a 3' overhang at one end of the molecule, The other end may be blunt-ended or have also an overhang (5' or 3'). When the siRNA molecule comprises an overhang at both ends of the molecule, the length of the overhangs may be the same or different. In one embodiment, the siRNA molecule of the present invention comprises 3' overhangs of about 1 to about 3 nucleotides on both ends of the molecule.

In some embodiments, an oligonucleotide may be a microRNA (miRNA). MicroRNAs (referred to as "miR-NAs") are small non-coding RNAs, belonging to a class of regulatory molecules found in plants and animals that control gene expression by binding to complementary sites on a target RNA transcript. miRNAs are generated from large RNA precursors (termed pri-miRNAs) that are processed in the nucleus into approximately 70 nucleotide pre-miRNAs, which fold into imperfect stem-loop structures (Lee, Y., et al., Nature (2003) 425(6956):415-9). The pre-miRNAs undergo an additional processing step within the cytoplasm where mature miRNAs of 18-25 nucleotides in length are excised from one side of the pre-miRNA hairpin by an RNase III enzyme, Dicer (Hutvagner, G., et al., Science (2001) 12:12 and Grishok, A., et al., Cell (2001) 106(1):23-34).

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides, although miRNAs of up to 2000 nucleotides can be utilized. In a preferred embodiment the size range of the miRNA is from 70 to 170 nucleotides in length. In another preferred embodiment, mature miRNAs of from 21 to 25 nucleotides in length can be used.

In some embodiments, the miRNA may be a miR-30 precursor. As used herein, an "miR-30 precursor", also called an miR-30 hairpin, is a precursor of the human microRNA miR-30, as it is understood in the literature (e.g., Zeng and Cullen, 2003; Zeng and Cullen, 2005; Zeng et al., 2005; United States Patent Application Publication No. US 2004/005341), where the precursor could be modified from the wild-type miR-30 precursor in any manner described or implied by that literature, while retaining the ability to be processed into an miRNA. In some embodiments, a miR-30 precursor is at least 80 nucleotides long and comprises a stem-loop structure. In some embodiments, the miR-30 precursor further comprises a first miRNA sequence of 20-22 nucleotides on the stem of the stem-loop structure complementary to a portion of a first target sequence (e.g., a sequence within a euchromatic region of a target gene disclosed herein).

A miRNA may be isolated from a variety of sources or may be synthesized according to methods well known in the art (see, e.g., Current Protocols in Molecular Biology, Wiley Online Library; U.S. Pat. No. 8,354,384; and Wahid et al. MicroRNAs: synthesis, mechanism, function, and recent clinical trials. Biochim Biophys Acta. 2010; 1803(11):1231-43). In some embodiments, a miRNA is expressed from a vector as known in the art or described herein. In some embodiments, the vector may include a sequence encoding a mature miRNA. In some embodiments, the vector may include a sequence encoding a pre-miRNA such that the pre-miRNA is expressed and processed in a cell into a mature miRNA. In some embodiments, the vector may include a sequence encoding a pri-miRNA. In this embodiment, the primary transcript is first processed to produce the stem-loop precursor miRNA molecule. The stem-loop precursor is then processed to produce the mature microRNA.

In some embodiments, oligonucleotides provided herein may be in the form of aptamers. An "aptamer" is any nucleic acid that binds specifically to a target, such as a small molecule, protein, nucleic acid, cell, tissue or organism. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof.

Selection of nucleic acid aptamers may be accomplished by any suitable method known in the art, including an optimized protocol for in vitro selection, known as SELEX (Systemic Evolution of Ligands by Exponential enrichment). Many factors are important for successful aptamer selection. For example, the target molecule should be stable and easily reproduced for each round of SELEX, because the SELEX process involves multiple rounds of binding, selection, and amplification to enrich the nucleic acid molecules. In addition, the nucleic acids that exhibit specific binding to the target molecule have to be present in the initial library. Thus, it is advantageous to produce a highly diverse nucleic acid pool. Because the starting library is not guaranteed to contain aptamers to the target molecule, the SELEX process for a single target may need to be repeated with different starting libraries. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3',5'-phosphate diester to a 2',3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (J. Am. Chem. Soc. (1993) 115:8483-8484) disclosed hammerhead-like molecules in which two of the base pairs of stem II, and all four of the nucleotides of loop II were replaced with non-nucleoside linkers based on hexaethylene glycol, propanediol, bis(tri-ethylene glycol) phosphate, tris(propanediol)bisphosphate, or bis(propanediol) phosphate. Ma et al. (Biochem. (1993) 32:1751-1758; Nucleic Acids Res. (1993) 21:2585-2589)

replaced the six nucleotide loop of the TAR ribozyme hairpin with non-nucleotidic, ethylene glycol-related linkers. Thomson et al. (Nucleic Acids Res. (1993) 21:5600-5603) replaced loop II with linear, non-nucleotidic linkers of 13, 17, and 19 atoms in length.

Ribozyme oligonucleotides can be prepared using well known methods (see, e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems, Inc. or Milligen. The ribozyme may also be produced in recombinant vectors by conventional means. See, Molecular Cloning: A Laboratory Manual, Cold Spring Harbor Laboratory (Current edition). The ribozyme RNA sequences may be synthesized conventionally, for example, by using RNA polymerases such as T7 or SP6.

Formulation, Delivery, and Dosing

The oligonucleotides described herein can be formulated for administration to a subject for treating a condition associated with decreased levels of a target gene. It should be understood that the formulations, compositions and methods can be practiced with any of the oligonucleotides disclosed herein.

The formulations may conveniently be presented in unit dosage form and may be prepared by any methods well known in the art of pharmacy. The amount of active ingredient (e.g., an oligonucleotide or compound of the invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g. tumor regression.

Pharmaceutical formulations of this invention can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

A formulated oligonucleotide composition can assume a variety of states. In some examples, the composition is at least partially crystalline, uniformly crystalline, and/or anhydrous (e.g., less than 80, 50, 30, 20, or 10% water). In another example, the oligonucleotide is in an aqueous phase, e.g., in a solution that includes water. The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the oligonucleotide composition is formulated in a manner that is compatible with the intended method of administration.

In some embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A oligonucleotide preparation can be formulated or administered (together or separately) in combination with another agent, e.g., another therapeutic agent or an agent that stabilizes an oligonucleotide, e.g., a protein that complexes with the oligonucleotide. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the oligonucleotide preparation includes another oligonucleotide, e.g., a second oligonucleotide that modulates expression of a second gene or a second oligonucleotide that modulates expression of the first gene. Still other preparation can include at least 3, 5, ten, twenty, fifty, or a hundred or more different oligonucleotide species. Such oligonucleotides can mediated gene expression with respect to a similar number of different genes. In one embodiment, the oligonucleotide preparation includes at least a second therapeutic agent (e.g., an agent other than an oligonucleotide).

Route of Delivery

A composition that includes an oligonucleotide can be delivered to a subject by a variety of routes. Exemplary routes include: intrathecal, intraneural, intracerebral, intramuscular, oral, intravenous, intradermal, topical, rectal, parenteral, anal, intravaginal, intranasal, pulmonary, or ocular. The term "therapeutically effective amount" is the amount of oligonucleotide present in the composition that is needed to provide the desired level of gene expression in the subject to be treated to give the anticipated physiological response. The term "physiologically effective amount" is that amount delivered to a subject to give the desired palliative or curative effect. The term "pharmaceutically acceptable carrier" means that the carrier can be administered to a subject with no significant adverse toxicological effects to the subject.

The oligonucleotide molecules of the invention can be incorporated into pharmaceutical compositions suitable for administration. Such compositions typically include one or more species of oligonucleotide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the oligonucleotide in aerosol form. The vascular endothelial cells could be targeted by coating a balloon catheter with the oligonucleotide and mechanically introducing the oligonucleotide. Targeting of neuronal cells could be accomplished by intrathecal, intraneural, intracerebral administration.

Topical administration refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy. In addition, iontophoresis (transfer of ionic solutes through biological membranes under the influence of an electric field), phonophoresis or sonophoresis (use of ultrasound to enhance the absorption of various therapeutic agents across biological membranes, notably the skin and the cornea), and optimization of vehicle characteristics relative to dose position and retention at the site of administration may be useful methods for enhancing the transport of topically applied compositions across skin and mucosal sites.

Both the oral and nasal membranes offer advantages over other routes of administration. For example, oligonucleotides administered through these membranes may have a rapid onset of action, provide therapeutic plasma levels, avoid first pass effect of hepatic metabolism, and avoid exposure of the oligonucleotides to the hostile gastrointestinal (GI) environment. Additional advantages include easy access to the membrane sites so that the oligonucleotide can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A pharmaceutical composition of oligonucleotide may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Compositions for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a tumor).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Any of the oligonucleotides described herein can be administered to ocular tissue. For example, the compositions can be applied to the surface of the eye or nearby tissue, e.g., the inside of the eyelid. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The oligonucleotide can also be administered to the interior of the eye, and can be introduced by a needle or other delivery device which can introduce it to a selected area or structure.

Pulmonary delivery compositions can be delivered by inhalation by the patient of a dispersion so that the composition, preferably oligonucleotides, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A oligonucleotide composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 µm in diameter preferably with a relatively uniform spheroidal shape distribution. More preferably the diameter is less than about 7.5 µm and most preferably less than about 5.0 µm. Usually the particle size distribution is between about 0.1 µm and about 5 µm in diameter, particularly about 0.3 µm to about 5 µm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar oligonucleotide formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to an oligonucleotide, e.g., a device can release insulin.

In one embodiment, unit doses or measured doses of a composition that includes oligonucleotide are dispensed by an implanted device. The device can include a sensor that monitors a parameter within a subject. For example, the device can include pump, e.g., and, optionally, associated electronics.

Tissue, e.g., cells or organs can be treated with an oligonucleotide, ex vivo and then administered or implanted in a subject. The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation. Introduction of treated tissue, whether autologous or transplant, can be combined with other therapies. In some implementations, the oligonucleotide treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

Dosage

In one aspect, the invention features a method of administering an oligonucleotide (e.g., as a compound or as a component of a composition) to a subject (e.g., a human subject). In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or disorder, e.g., a disease or disorder associated with a reduced level of a target gene. The unit dose, for example, can be administered by injection (e.g., intravenous or intramuscular), an inhaled dose, or a topical application.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of an oligonucleotide. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the oligonucleotide may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, oligonucleotide pharmaceutical compositions are provided that include a plurality of oligonucleotides. In some embodiments, oligonucleotides in the plurality have sequences that are non-overlapping and non-adjacent to other oligonucleotides in the plurality with respect to a target gene sequence. In some embodiments, the plurality contains oligonucleotides specific for different target genes. In some embodiments, the plurality contains oligonucleotides that are allele specific.

In some cases, a patient is treated with an oligonucleotide in conjunction with other therapeutic modalities.

Following successful treatment, it may be desirable to have the patient undergo maintenance therapy to prevent the recurrence of the disease state, wherein the compound of the invention is administered in maintenance doses, ranging from 0.0001 mg to 100 mg per kg of body weight.

The concentration of the oligonucleotide composition is an amount sufficient to be effective in treating or preventing a disorder or to regulate a physiological condition in humans. The concentration or amount of oligonucleotide administered will depend on the parameters determined for the agent and the method of administration, e.g. nasal, buccal, pulmonary. For example, nasal formulations may tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an oligonucleotide can include a single treatment or, preferably, can include a series of treatments. It will also be appreciated that the effective dosage of an oligonucleotide used for treatment may increase or decrease over the course of a particular treatment. For example, the subject can be monitored after administering an oligonucleotide composition. Based on information from the monitoring, an additional amount of the oligonucleotide composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of gene expression levels in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that are engineered to express a human gene. In another embodiment, the composition for testing includes an oligonucleotide that is complementary, at least in an internal region, to a sequence that is conserved between gene in the animal model and the corresponding gene in a human.

In one embodiment, the administration of the oligonucleotide composition is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The composition can be provided in measured doses or in a dispenser which delivers a metered dose. Selected modes of delivery are discussed in more detail below.

Kits

In certain aspects of the invention, kits are provided, comprising a container housing a composition comprising an oligonucleotide. In some embodiments, the composition is a pharmaceutical composition comprising an oligonucleotide and a pharmaceutically acceptable carrier. In some embodiments, the individual components of the pharmaceutical composition may be provided in one container. Alternatively, it may be desirable to provide the components of the pharmaceutical composition separately in two or more containers, e.g., one container for oligonucleotides, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The present invention is further illustrated by the following Examples, which in no way should be construed as further limiting.

EXAMPLES

Example 1. Exemplary Target Euchromatin Region and Oligonucleotides Designed to be Complementary to the Region Introduction An exemplary target euchromatin region is the region encompassing the overlap of minus-strand RNA transcript I and euchromatic region III as shown in FIG. 1. Oligonucleotides were then designed to be complementary to a portion of the plus-strand or the minus-strand of a target euchromatin region of FXN (FIG. 1). Without wishing to be bound by theory, it was hypothesized that these oligonucleotides may function by binding (a) to the DNA of the target euchromatin region, thus modulating transcription of the antisense RNA, (b) to the antisense RNA, resulting in either degradation of the antisense RNA and/or inhibition of the function of the antisense RNA (e.g., by blocking hybridization of the antisense RNA transcript with the sense RNA transcript), or (c) to both the DNA and the antisense RNA.

Materials and Methods:

Identification of Target Euchromatin Regions of FXN

Target euchromatin regions were identified as regions within the FXN gene where antisense RNA transcription occurs and open chromatin is present, as indicated by FAIRE or DNaseI hypersensitivity. The low levels of antisense RNA transcription were identified using cap analysis gene expression (CAGE). In particular, DNaseI Hypersensitivity by Digital DNaseI from ENCODE/University of Washington, DNaseI Digital Genomic Footprinting from ENCODE/University of Washington, Open Chromatin by FAIRE from ENCODE/OpenChrom(UNC Chapel Hill) and DNaseI Hypersensitivity Uniform Peaks from ENCODE/Analysis databases were examined. To explore evidence of RNA in DNaseI sensitive locations, CSHL Long RNA-Seq, Caltech RNA-seq and RIKEN CAGE data were examined. Since boundaries of RNAs were determined, regions overlapping raw CAGE and RNAseq reads were used for targeting of oligos.

Real Time PCR

RNA analysis, cDNA synthesis and QRT-PCR was done with Life Technologies Cells-to-Ct kit and StepOne Plus instrument. Baseline levels were also determined for mRNA of various housekeeping genes which are constitutively expressed. A "control" housekeeping gene with approximately the same level of baseline expression as the target gene was chosen for comparison purposes.

ELISA

ELISA assays were performed as previously described using the Abcam Frataxin ELISA kit (ab115346).

Cell Lines

Cells were cultured using conditions known in the art and as suggested by the Coriell Cell Repository (see, e.g., Current Protocols in Cell Biology). Details of the cell lines used in the experiments described herein are provided in Table 2.

TABLE 2

| Cell lines | | | | |
|---|---|---|---|---|
| Cell lines | Clinically affected | Cell type | # of GAA repeats | Notes |
| GM03816 | Y | Fibroblast | 330/380 | Coriell Cell Repository |

Oligonucleotide Design

Oligonucleotides were designed to be complementary to a target euchromatin region of FXN. The sequence and structure of each oligonucleotide is shown in Table 3 and Table 4. Table 5 provides a description of the nucleotide analogs, modifications and internucleoside linkages used for certain oligonucleotides described in Table 3 and Table 4 and Table 6.

TABLE 3

Oligonucleotides complementary to a target euchromatin region of FXN

| SEQ ID NO | Oligo Name | Base Sequence | Gene Name | Organism | Formatted Sequence |
|---|---|---|---|---|---|
| 1 | 400 | TTTTTCATTTTC CCTCCTGG | FXN | human | dTs;InaTs;dTs;InaTs;dTs;InaCs;dAs;InaTs;dTs; InaTs;dTs;InaCs;dCs;InaCs;dTs;InaCs;dCs;InaTs; dGs;InaG-Sup |
| 2 | 401 | TTTTTGTAGGC TACCCTTTA | FXN | human | dTs;InaTs;dTs;InaTs;dTs;InaGs;dTs;InaAs;dGs; InaGs;dCs;InaTs;dAs;InaCs;dCs;InaCs;dTs;InaTs; dTs;InaA-Sup |
| 3 | 402 | TTTTTGAGGCT TGTTGCTTT | FXN | human | dTs;InaTs;dTs;InaTs;dTs;InaGs;dAs;InaGs;dGs; InaCs;dTs;InaTs;dGs;InaTs;dTs;InaGs;dCs;InaTs; dTs;InaT-Sup |
| 4 | 403 | TTTTTCATGTA TGATGTTAT | FXN | human | dTs;InaTs;dTs;InaTs;dTs;InaCs;dAs;InaTs;dGs; InaTs;dAs;InaTs;dGs;InaAs;dTs;InaGs;dTs;InaTs; dAs;InaT-Sup |
| 5 | 404 | AAAGCCTTAA AAACC | FXN | human | dAs;InaAs;dAs;InaGs;dCs;InaCs;dTs;InaTs;dAs; InaAs;dAs;InaAs;dAs;InaCs;dC-Sup |
| 6 | 405 | TCAGGCCAAG ACCCC | FXN | human | dTs;InaCs;dAs;InaGs;dGs;InaCs;dCs;InaAs;dAs; InaGs;dAs;InaCs;dCs;InaCs;dC-Sup |
| 7 | 406 | CCCAGCTTCAT TATG | FXN | human | dCs;InaCs;dCs;InaAs;dGs;InaCs;dTs;InaTs;dCs; InaAs;dTs;InaTs;dAs;InaTs;dG-Sup |
| 8 | 407 | AATGTGTTGCC TCCT | FXN | human | dAs;InaAs;dTs;InaGs;dTs;InaGs;dTs;InaTs;dGs; InaCs;dCs;InaTs;dCs;InaCs;dT-Sup |
| 9 | 408 | AAAAAGCAAA ATAAT | FXN | human | dAs;InaAs;dAs;InaAs;dAs;InaGs;dCs;InaAs;dAs; InaAs;dAs;InaTs;dAs;InaAs;dT-Sup |
| 10 | 409 | CCAGGAGGGA AAATG | FXN | human | dCs;InaCs;dAs;InaGs;dGs;InaAs;dGs;InaGs;dGs; InaAs;dAs;InaAs;dAs;InaTs;dG-Sup |
| 11 | 410 | TAAAGGGTAG CCTAC | FXN | human | dTs;InaAs;dAs;InaAs;dGs;InaGs;dGs;InaTs;dAs; InaGs;dCs;InaCs;dTs;InaAs;dC-Sup |
| 12 | 411 | AAAGCAACAA GCCTC | FXN | human | dAs;InaAs;dAs;InaGs;dCs;InaAs;dAs;InaCs;dAs; InaAs;dGs;InaCs;dCs;InaTs;dC-Sup |
| 13 | 412 | ATAACATCATA CATG | FXN | human | dAs;InaTs;dAs;InaAs;dCs;InaAs;dTs;InaCs;dAs; InaTs;dAs;InaCs;dAs;InaTs;dG-Sup |
| 14 | 413 | GATACTATCTT CCTC | FXN | human | dGs;InaAs;dTs;InaAs;dCs;InaTs;dAs;InaTs;dCs; InaTs;dTs;InaCs;dCs;InaTs;dC-Sup |
| 15 | 414 | ATGGGGACG GGGCA | FXN | human | dAs;InaTs;dGs;InaGs;dGs;InaGs;dGs;InaAs;dCs; InaGs;dGs;InaGs;dGs;InaCs;dA-Sup |
| 16 | 415 | GGTTGAGACT GGGTG | FXN | human | dGs;InaGs;dTs;InaTs;dGs;InaAs;dGs;InaAs;dCs; InaTs;dGs;InaGs;dGs;InaTs;dG-Sup |

TABLE 3-continued

Oligonucleotides complementary to
a target euchromatin region of FXN

| SEQ ID NO | Oligo Name | Base Sequence | Gene Name | Organism | Formatted Sequence |
|---|---|---|---|---|---|
| 17 | 416 | AGACTGAAGAGGTGC | FXN | human | dAs;InaGs;dAs;InaCs;dTs;InaGs;dAs;InaAs;dGs;InaAs;dGs;InaGs;dTs;InaGs;dC-Sup |
| 18 | 417 | CGGGACGGCTGTGTT | FXN | human | dCs;InaGs;dGs;InaGs;dAs;InaCs;dGs;InaGs;dCs;InaTs;dGs;InaTs;dGs;InaTs;dT-Sup |
| 19 | 418 | TCTGTGTGGGCAGCA | FXN | human | dTs;InaCs;dTs;InaGs;dTs;InaGs;dTs;InaGs;dGs;InaGs;dCs;InaAs;dGs;InaCs;dA-Sup |
| 20 | 419 | AAAGCCTTAAAAACC | FXN | human | InaAs;InaAs;InaAs;dGs;dCs;dCs;dTs;dTs;dAs;dAs;dAs;dAs;InaAs;InaCs;InaC-Sup |
| 21 | 420 | TCAGGCCAAGACCCC | FXN | human | InaTs;InaCs;InaAs;dGs;dGs;dCs;dCs;dAs;dAs;dGs;dAs;dCs;InaCs;InaCs;InaC-Sup |
| 22 | 421 | CCCAGCTTCATTATG | FXN | human | InaCs;InaCs;InaCs;dAs;dGs;dCs;dTs;dTs;dCs;dAs;dTs;dTs;InaAs;InaTs;InaG-Sup |
| 23 | 422 | AATGTGTTGCCTCCT | FXN | human | InaAs;InaAs;InaTs;dGs;dTs;dGs;dTs;dGs;dCs;dCs;dTs;InaCs;InaCs;InaT-Sup |
| 24 | 423 | AAAAAGCAAAATAAT | FXN | human | InaAs;InaAs;InaAs;dAs;dAs;dGs;dCs;dAs;dAs;dAs;dAs;dTs;InaAs;InaAs;InaT-Sup |
| 25 | 424 | CCAGGAGGGAAAATG | FXN | human | InaCs;InaCs;InaAs;dGs;dGs;dAs;dGs;dGs;dGs;dAs;dAs;dAs;InaAs;InaTs;InaG-Sup |
| 26 | 425 | TAAAGGGTAGCCTAC | FXN | human | InaTs;InaAs;InaAs;dAs;dGs;dGs;dGs;dTs;dAs;dGs;dCs;dCs;InaTs;InaAs;InaC-Sup |
| 27 | 426 | AAAGCAACAAGCCTC | FXN | human | InaAs;InaAs;InaAs;dGs;dCs;dAs;dAs;dCs;dAs;dAs;dGs;dCs;InaCs;InaTs;InaC-Sup |
| 28 | 427 | ATAACATCATACATG | FXN | human | InaAs;InaTs;InaAs;dAs;dCs;dAs;dTs;dCs;dAs;dTs;dAs;dCs;InaAs;InaTs;InaG-Sup |
| 29 | 428 | GATACTATCTTCCTC | FXN | human | InaGs;InaAs;InaTs;dAs;dCs;dTs;dAs;dTs;dCs;dTs;dTs;dCs;InaCs;InaTs;InaC-Sup |
| 30 | 429 | ATGGGGGACGGGGCA | FXN | human | InaAs;InaTs;InaGs;dGs;dGs;dGs;dGs;dAs;dCs;dGs;dGs;dGs;InaGs;InaCs;InaA-Sup |
| 31 | 430 | GGTTGAGACTGGGTG | FXN | human | InaGs;InaGs;InaTs;dTs;dGs;dAs;dGs;dAs;dCs;dTs;dGs;dGs;InaGs;InaTs;InaG-Sup |
| 32 | 431 | AGACTGAAGAGGTGC | FXN | human | InaAs;InaGs;InaAs;dCs;dTs;dGs;dAs;dAs;dGs;dAs;dGs;dGs;InaTs;InaGs;InaC-Sup |
| 33 | 432 | CGGGACGGCTGTGTT | FXN | human | InaCs;InaGs;InaGs;dGs;dAs;dCs;dGs;dGs;dCs;dTs;dGs;dTs;InaGs;InaTs;InaT-Sup |
| 34 | 433 | TCTGTGTGGGCAGCA | FXN | human | InaTs;InaCs;InaTs;dGs;dTs;dGs;dTs;dGs;dGs;dGs;dCs;dAs;InaGs;InaCs;InaA-Sup |

TABLE 4

Other oligonucleotides
designed to upregulate FXN

| SEQ ID NO | Oligo Name | Base Sequence | Gene Name | Organism | Formatted Sequence |
|---|---|---|---|---|---|
| 35 | 51 | CGCCCTCCAGCGCTG | FXN | human | dCs;InaGs;dCs;InaCs;dCs;InaTs;dCs;InaCs;dAs;InaGs;dCs;InaGs;dCs;InaTs;dG-Sup |
| 36 | 52 | CGCTCCGCCCTCCAG | FXN | human | dCs;InaGs;dCs;InaTs;dCs;InaCs;dGs;InaCs;dCs;InaCs;dTs;InaCs;dCs;InaAs;dG-Sup |

TABLE 4-continued

Other oligonucleotides designed to upregulate FXN

| SEQ ID NO | Oligo Name | Base Sequence | Gene Name | Organism | Formatted Sequence |
|---|---|---|---|---|---|
| 37 | 56 | CGCCCTCCAGCGCTGCC | FXN | human | dCs;lnaGs;dCs;lnaCs;dCs;lnaTs;dCs;lnaCs;dAs;lnaGs;dCs;lnaGs;dCs;lnaTs;dGs;lnaCs;dC-Sup |
| 38 | 57 | CGCTCCGCCCTCCAGCC | FXN | human | dCs;lnaGs;dCs;lnaTs;dCs;lnaCs;dGs;lnaCs;dCs;lnaCs;dTs;lnaCs;dCs;lnaAs;dGs;lnaCs;dC-Sup |
| 39 | 61 | CGCCCTCCAGCGCTGGGAAACCTC | FXN | human | dCs;lnaGs;dCs;lnaCs;dCs;lnaTs;dCs;lnaCs;dAs;lnaGs;dCs;lnaGs;dCs;lnaTs;dGs;lnaGs;dGs;dAs;dAs;dAs;dCs;lnaCs;dTs;lnaC-Sup |
| 40 | 62 | CGCTCCGCCCTCCAGCCAAAGGTC | FXN | human | dCs;lnaGs;dCs;lnaTs;dCs;lnaCs;dGs;lnaCs;dCs;lnaCs;dTs;lnaCs;dCs;lnaAs;dGs;lnaCs;dCs;dAs;dAs;dAs;dGs;lnaGs;dTs;lnaC-Sup |
| 41 | 73 | TTTTTGGGGTCTTGGCCTGA | FXN | human | dTs;lnaTs;dTs;lnaTs;dTs;lnaGs;dGs;lnaGs;dGs;lnaTs;dCs;lnaTs;dTs;lnaGs;dGs;lnaCs;dCs;lnaTs;dGs;lnaA-Sup |
| 42 | 75 | TTTTTAGGAGGCAACACATT | FXN | human | dTs;lnaTs;dTs;lnaTs;dTs;lnaAs;dGs;lnaGs;dAs;lnaGs;dGs;lnaCs;dAs;lnaAs;dCs;lnaAs;dCs;lnaAs;dTs;lnaT-Sup |
| 43 | 324 | CGGCGCCCGAGAGTCCACAT | FXN | human | dCs;lnaGs;dGs;lnaCs;dGs;lnaCs;dCs;lnaCs;dGs;lnaAs;dGs;lnaAs;dGs;lnaTs;dCs;lnaCs;dAs;lnaCs;dAs;lnaT-Sup |
| 44 | 329 | ACGGCGGCCGCAGAGTGGGG | FXN | human | dAs;lnaCs;dGs;lnaGs;dCs;lnaGs;dGs;lnaCs;dCs;lnaGs;dCs;lnaAs;dGs;lnaAs;dGs;lnaTs;dGs;lnaGs;dGs;lnaG-Sup |
| 45 | 359 | CCTCAAAAGCAGGAATAAAAAAATA | FXN | human | dCs;lnaCs;dTs;lnaCs;dAs;lnaAs;dAs;lnaAs;dGs;lnaCs;dAs;lnaGs;dGs;lnaAs;dAs;lnaTs;dAs;lnaAs;dAs;lnaAs;dAs;lnaAs;dAs;lnaAs;dTs;lnaA-Sup |

TABLE 5

Oligonucleotide Modifications

| Symbol | Feature Description |
|---|---|
| bio | 5' biotin |
| dAs | DNA w/3' thiophosphate |
| dCs | DNA w/3' thiophosphate |
| dGs | DNA w/3' thiophosphate |
| dTs | DNA w/3' thiophosphate |
| dG | DNA |
| enaAs | ENA w/ 3' thiophosphate |
| enaCs | ENA w/3' thiophosphate |
| enaGs | ENA w/3' thiophosphate |
| enaTs | ENA w/3' thiophosphate |
| fluAs | 2'-fluoro w/3' thiophosphate |
| fluCs | 2'-fluoro w/3' thiophosphate |
| fluGs | 2'-fluoro w/3' thiophosphate |
| fluUs | 2'-fluoro w/3' thiophosphate |
| lnaAs | LNA w/3' thiophosphate |
| lnaCs | LNA w/3' thiophosphate |
| lnaGs | LNA w/3' thiophosphate |
| lnaTs | LNA w/3' thiophosphate |
| omeAs | 2'-OMe w/3' thiophosphate |
| omeCs | 2'-OMe w/3' thiophosphate |
| omeGs | 2'-OMe w/3' thiophosphate |
| omeTs | 2'-OMe w/3' thiophosphate |
| lnaAs-Sup | LNA w/3' thiophosphate at 3' terminus |
| lnaCs-Sup | LNA w/3' thiophosphate at 3' terminus |
| lnaGs-Sup | LNA w/3' thiophosphate at 3' terminus |
| lnaTs-Sup | LNA w/3' thiophosphate at 3' terminus |
| lnaA-Sup | LNA w/3' OH at 3' terminus |
| lnaC-Sup | LNA w/3' OH at 3' terminus |
| lnaG-Sup | LNA w/3' OH at 3' terminus |
| lnaT-Sup | LNA w/3' OH at 3' terminus |
| omeA-Sup | 2'-OMe w/3' OH at 3' terminus |
| omeC-Sup | 2'-OMe w/3' OH at 3' terminus |
| omeG-Sup | 2'-OMe w/3' OH at 3' terminus |
| omeU-Sup | 2'-OMe w/3' OH at 3' terminus |
| dAs-Sup | DNA w/3' thiophosphate at 3' terminus |
| dCs-Sup | DNA w/3' thiophosphate at 3' terminus |
| dGs-Sup | DNA w/3' thiophosphate at 3' terminus |
| dTs-Sup | DNA w/3' thiophosphate at 3' terminus |
| dA-Sup | DNA w/3' OH at 3' terminus |
| dC-Sup | DNA w/3' OH at 3' terminus |
| dG-Sup | DNA w/3' OH at 3' terminus |
| dT-Sup | DNA w/3' OH at 3' terminus |

In Vitro Transfection of Cells with Oligonucleotides

Cells were seeded into each well of 24-well plates at a density of 25,000 cells per 500 uL and transfections were performed with Lipofectamine and the oligonucleotides. Control wells contained Lipofectamine alone. At time points post-transfection, approximately 200 uL of cell culture supernatants were stored at −80 C for ELISA and RNA was harvested from another aliquot of cells and quantitative PCR was carried out as outlined above. The percent induction of FXN mRNA expression by each oligonucleotide was determined by normalizing mRNA levels in the presence of the oligonucleotide to the mRNA levels in the presence of control (Lipofectamine alone).

Figure 2:
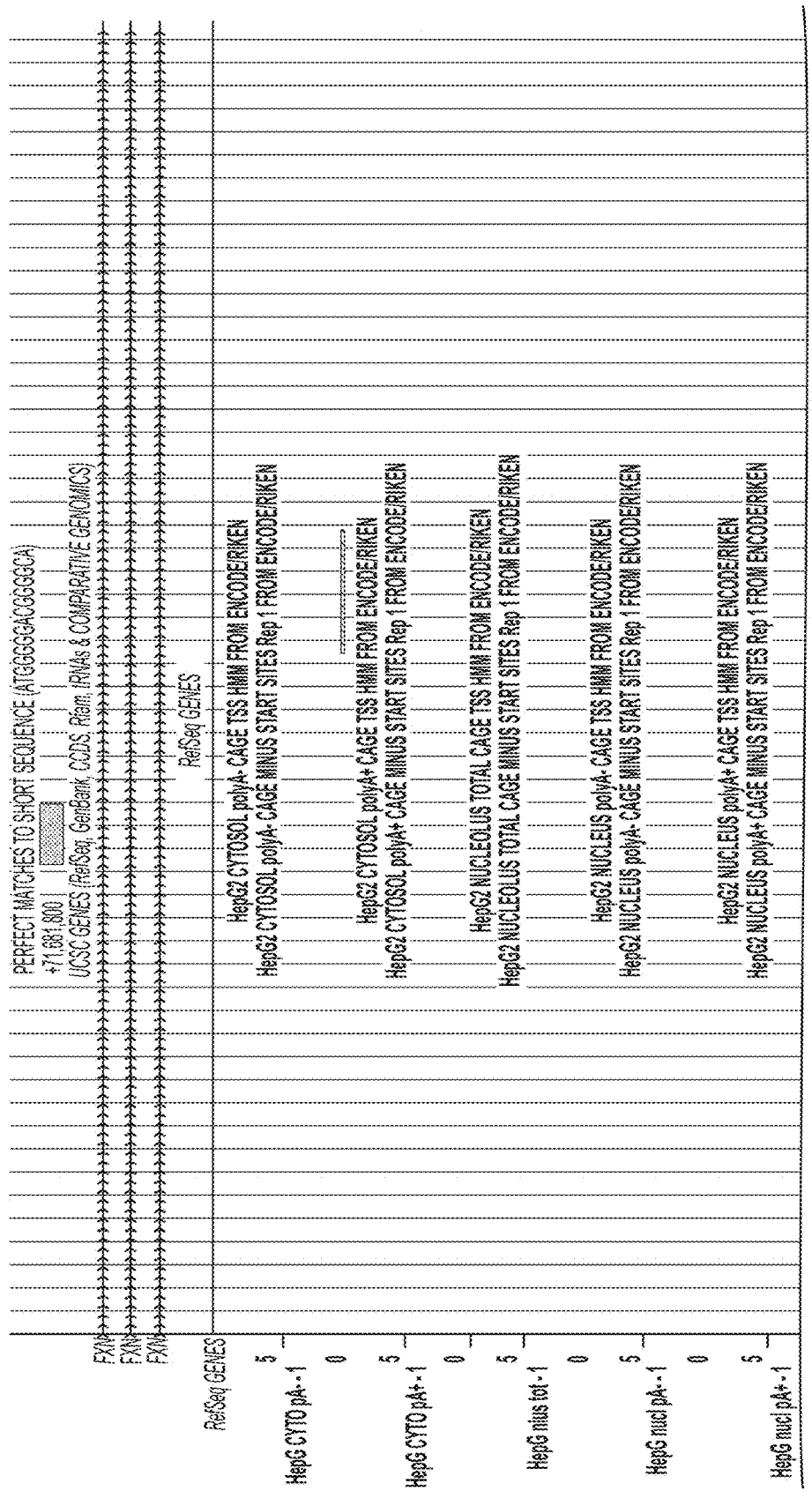
FIG. 2 is a diagram showing CAGE data, DNAaseI hypersensitivity data, and FAIRE data within the FXN locus on the UCSC genome browser. The black box indicates a region of complementarity with oligonucleotides 414 and 429.
Figure 2:
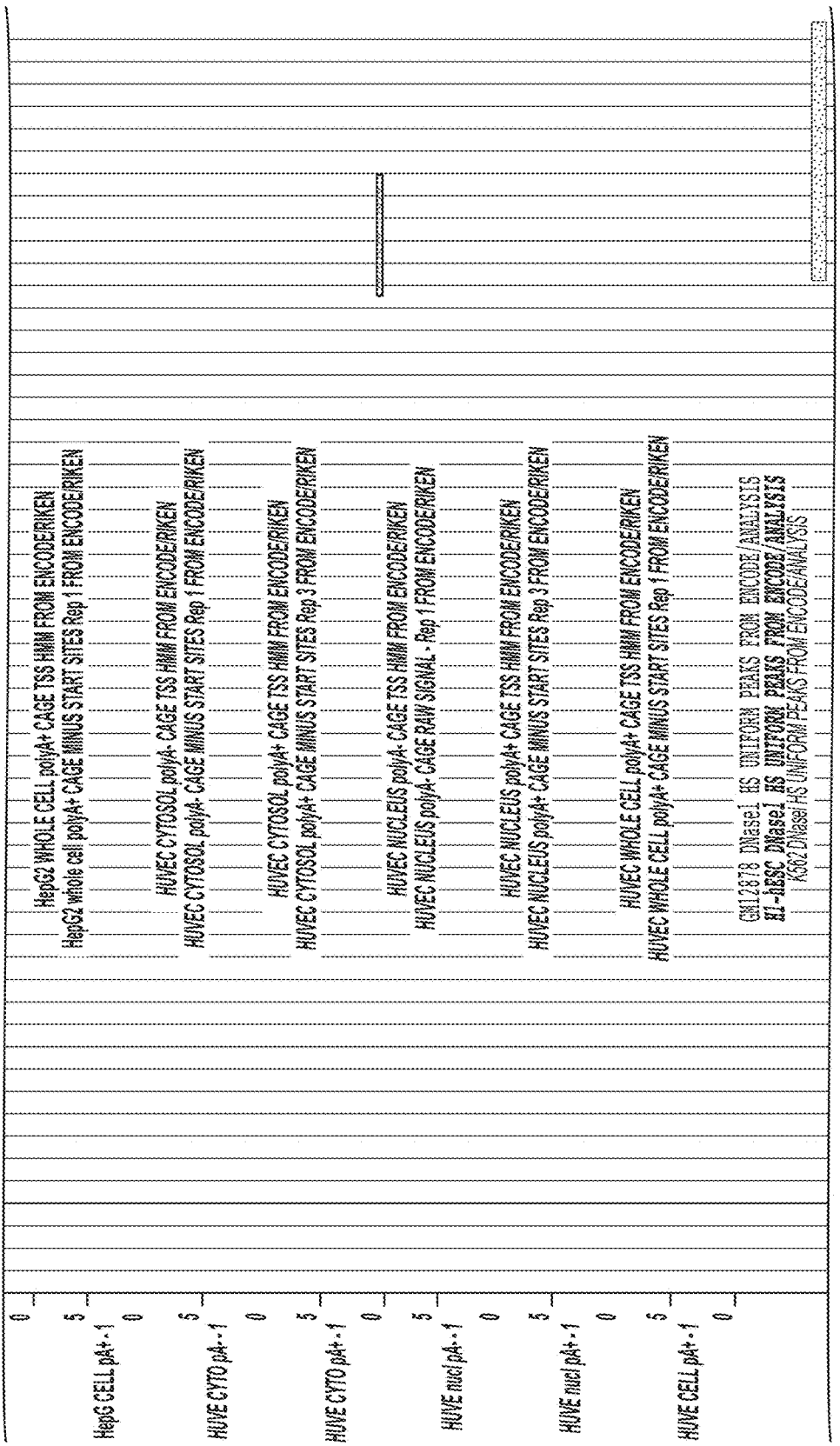
Figure 2:
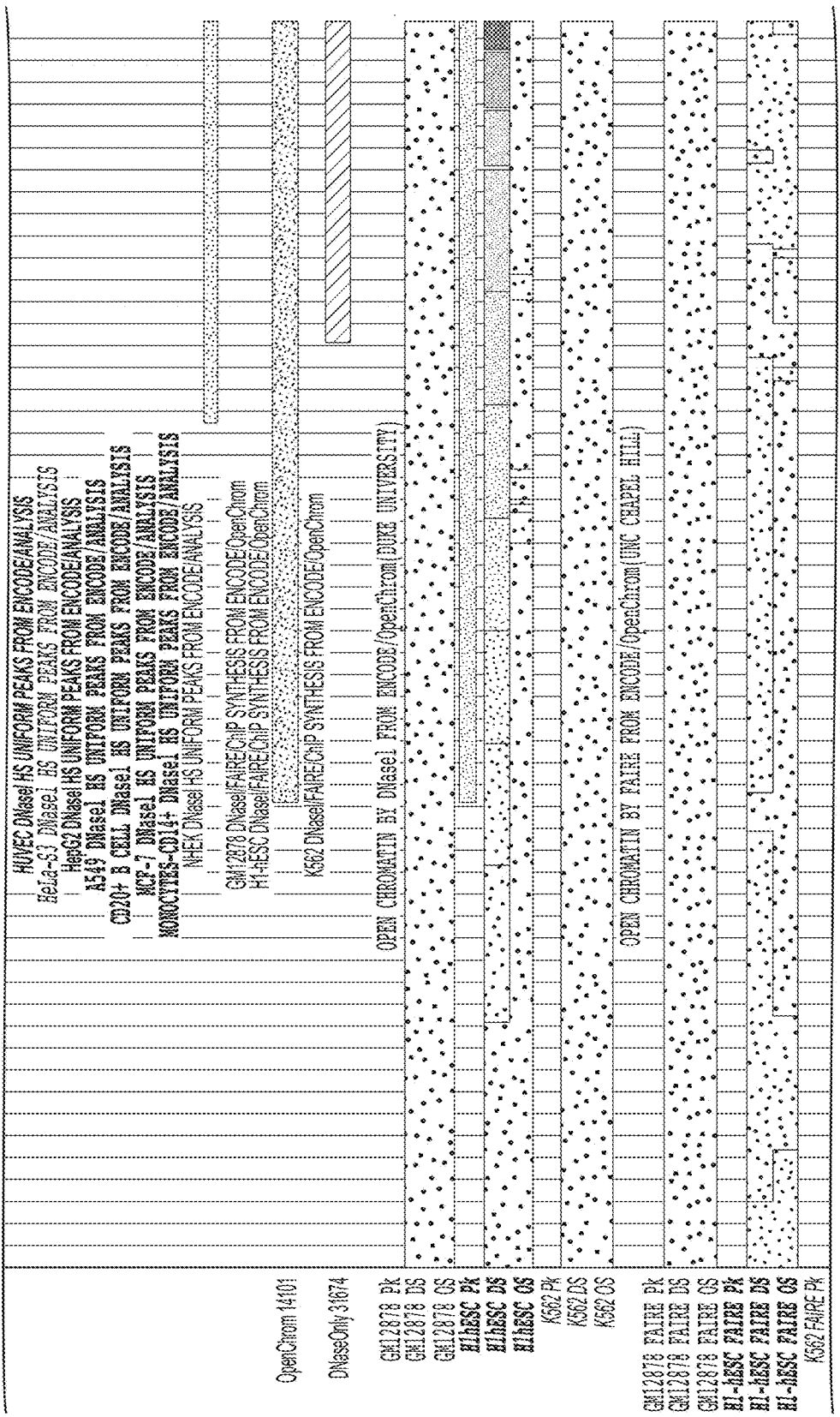
Figure 2:
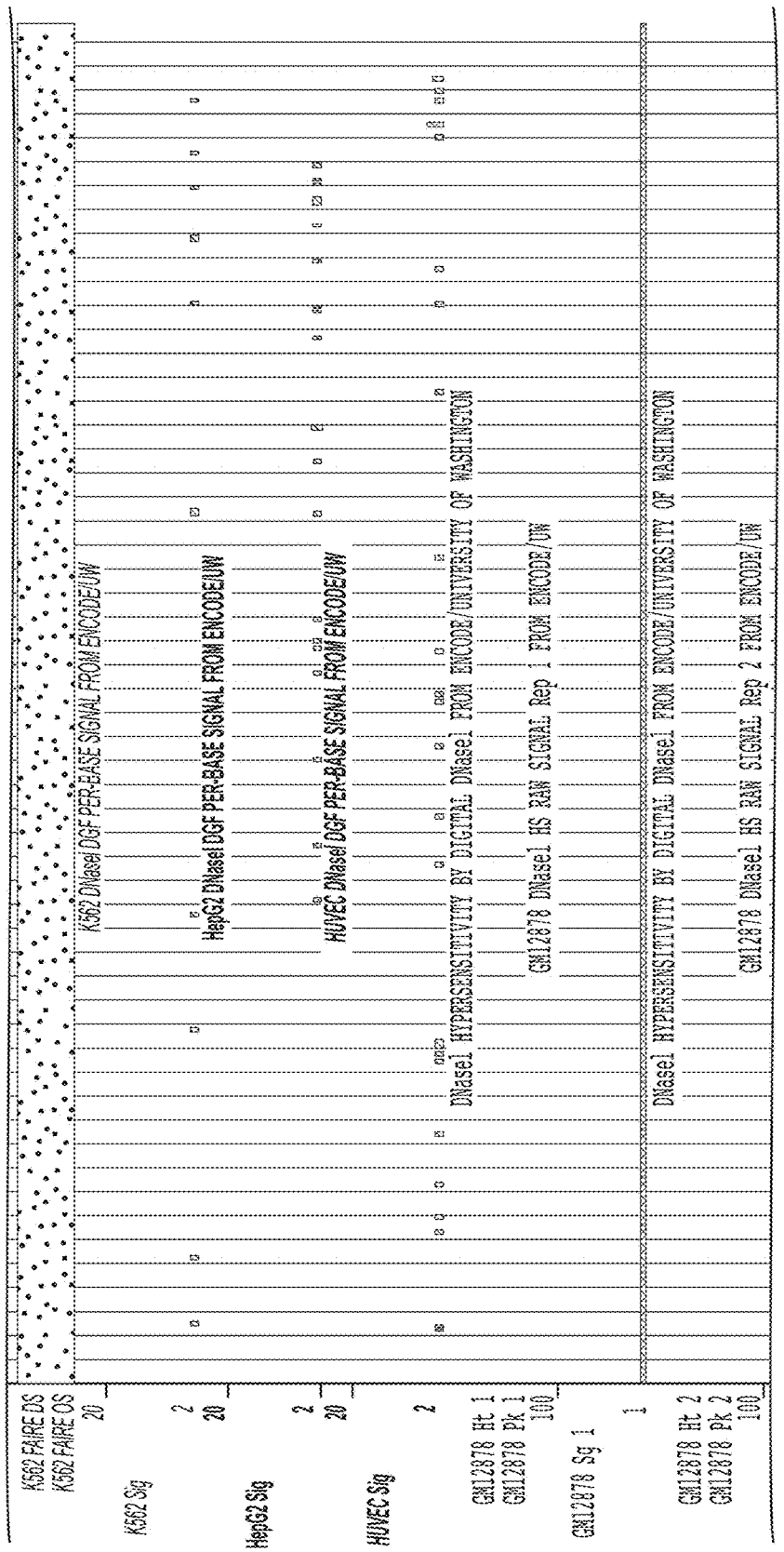
Figure 2:
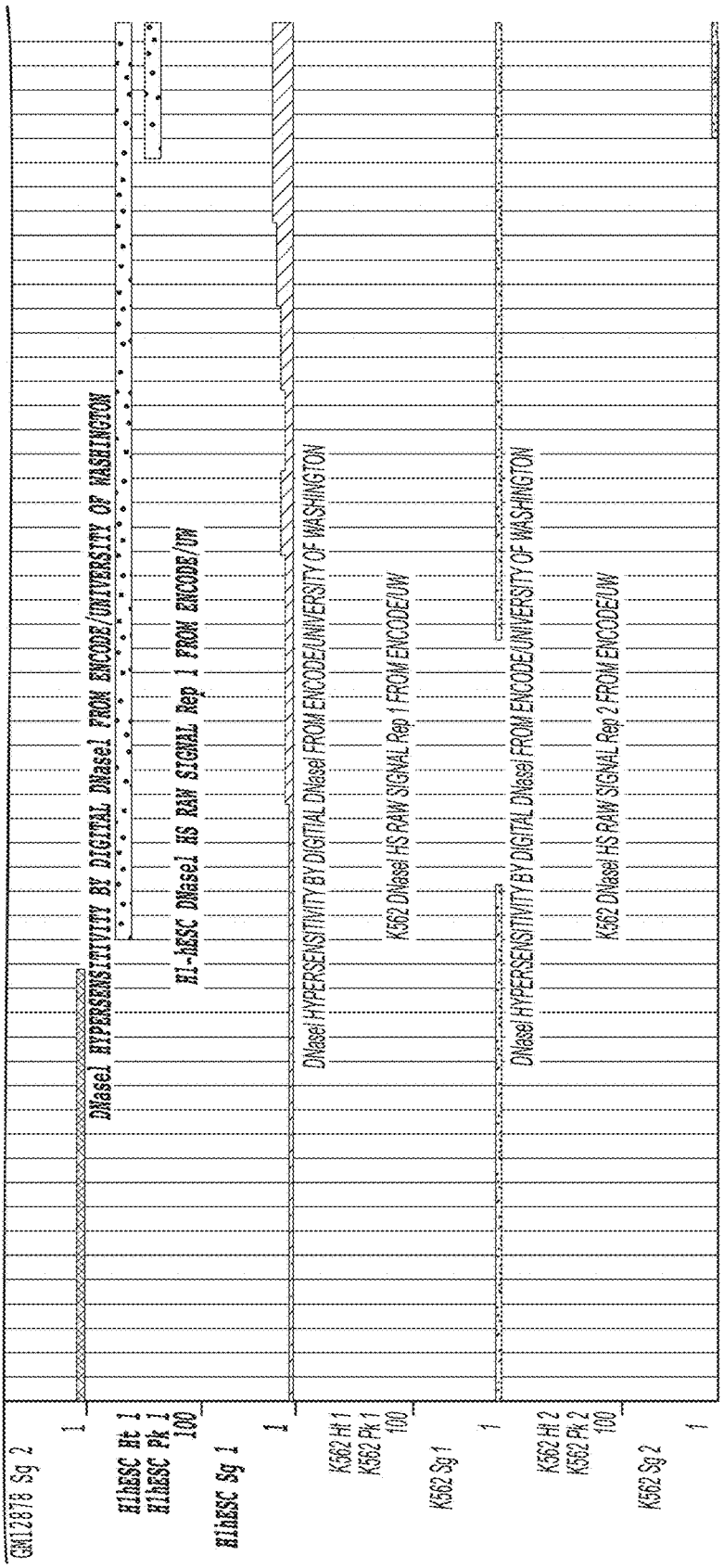
Figure 3:
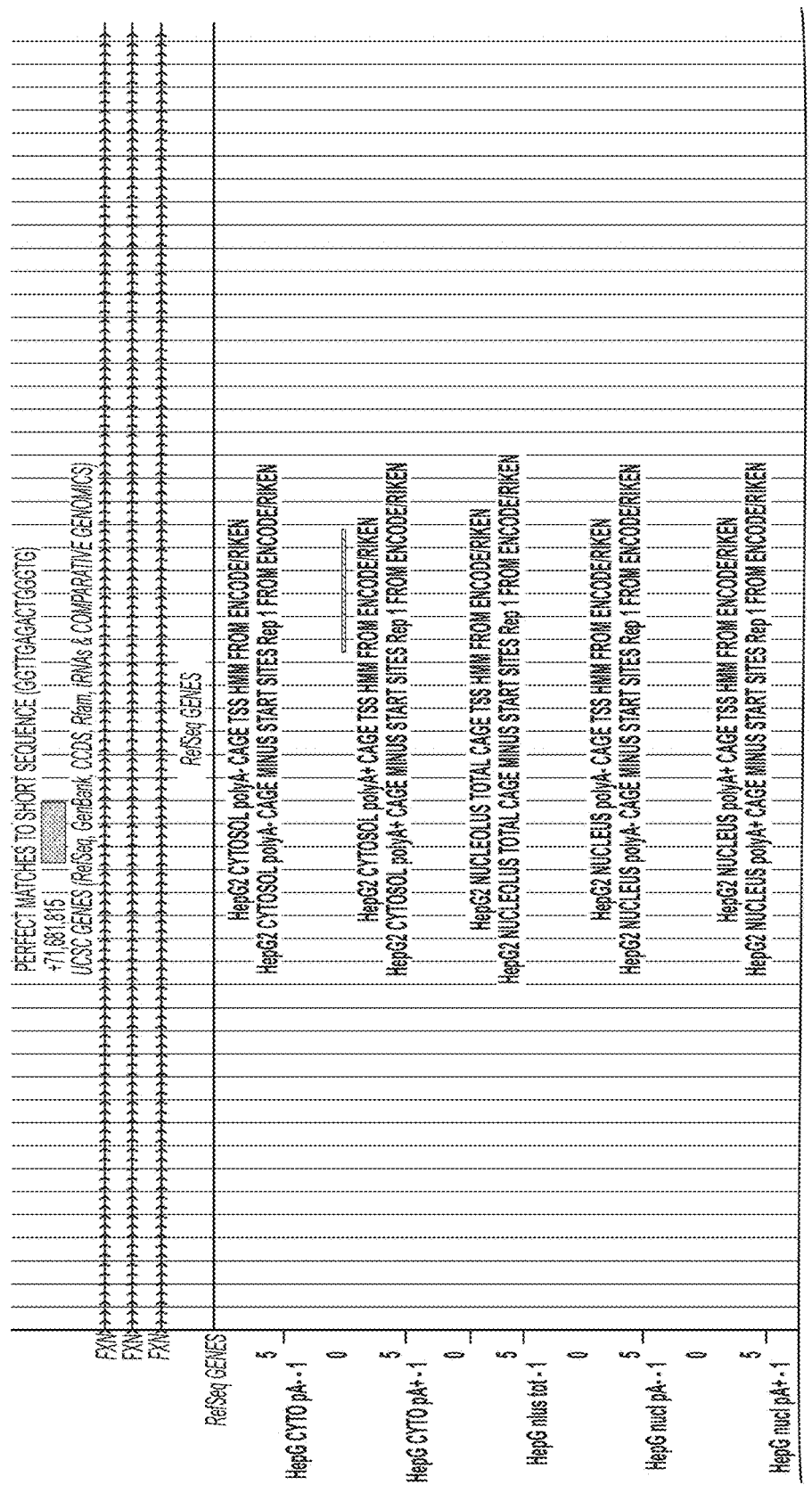
FIG. 3 is a diagram showing CAGE data, DNAaseI hypersensitivity data, and FAIRE data within the FXN locus on the UCSC genome browser. The black box indicates a region of complementarity with oligonucleotide 415.
Figure 3:
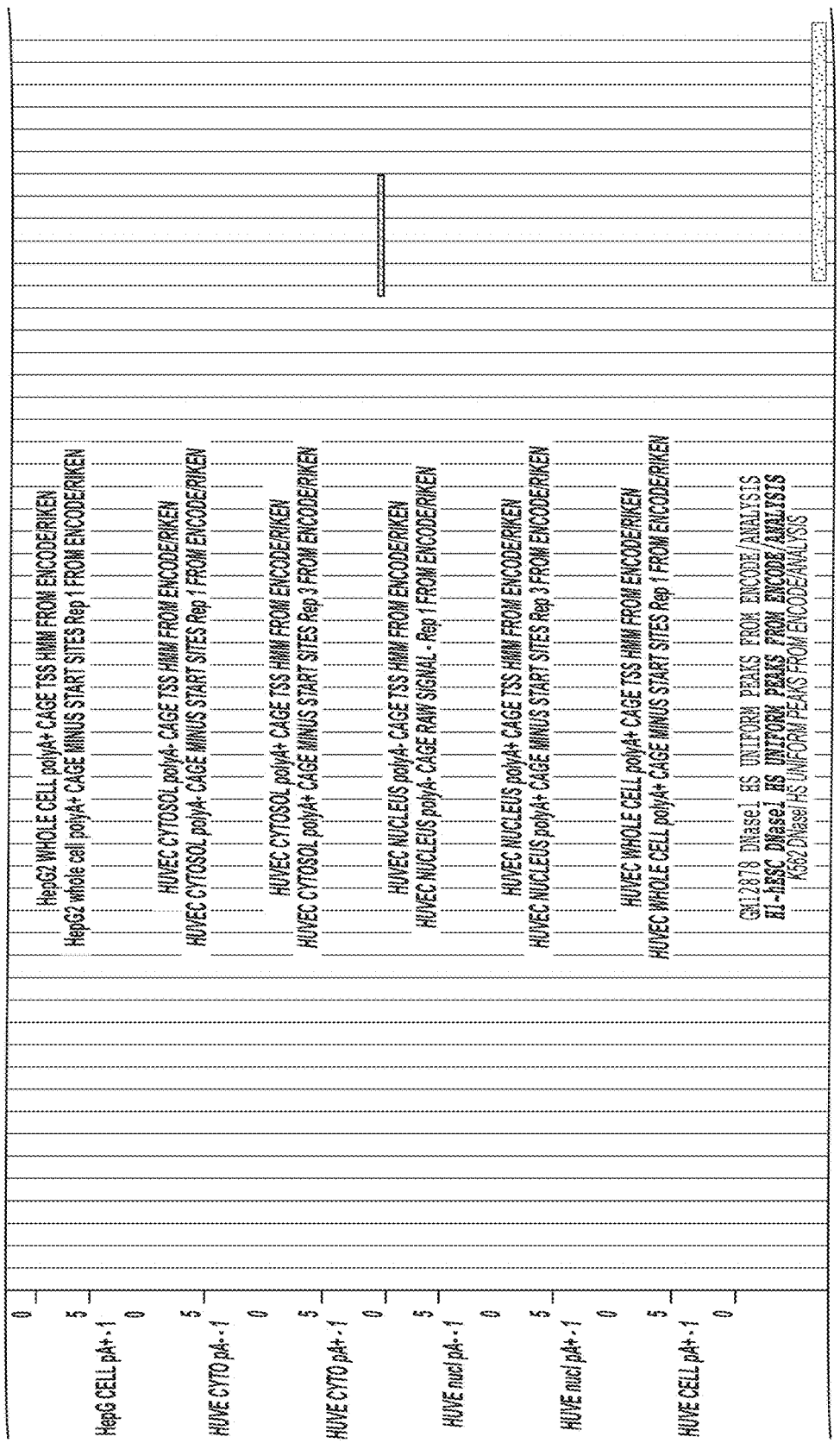
Figure 3:
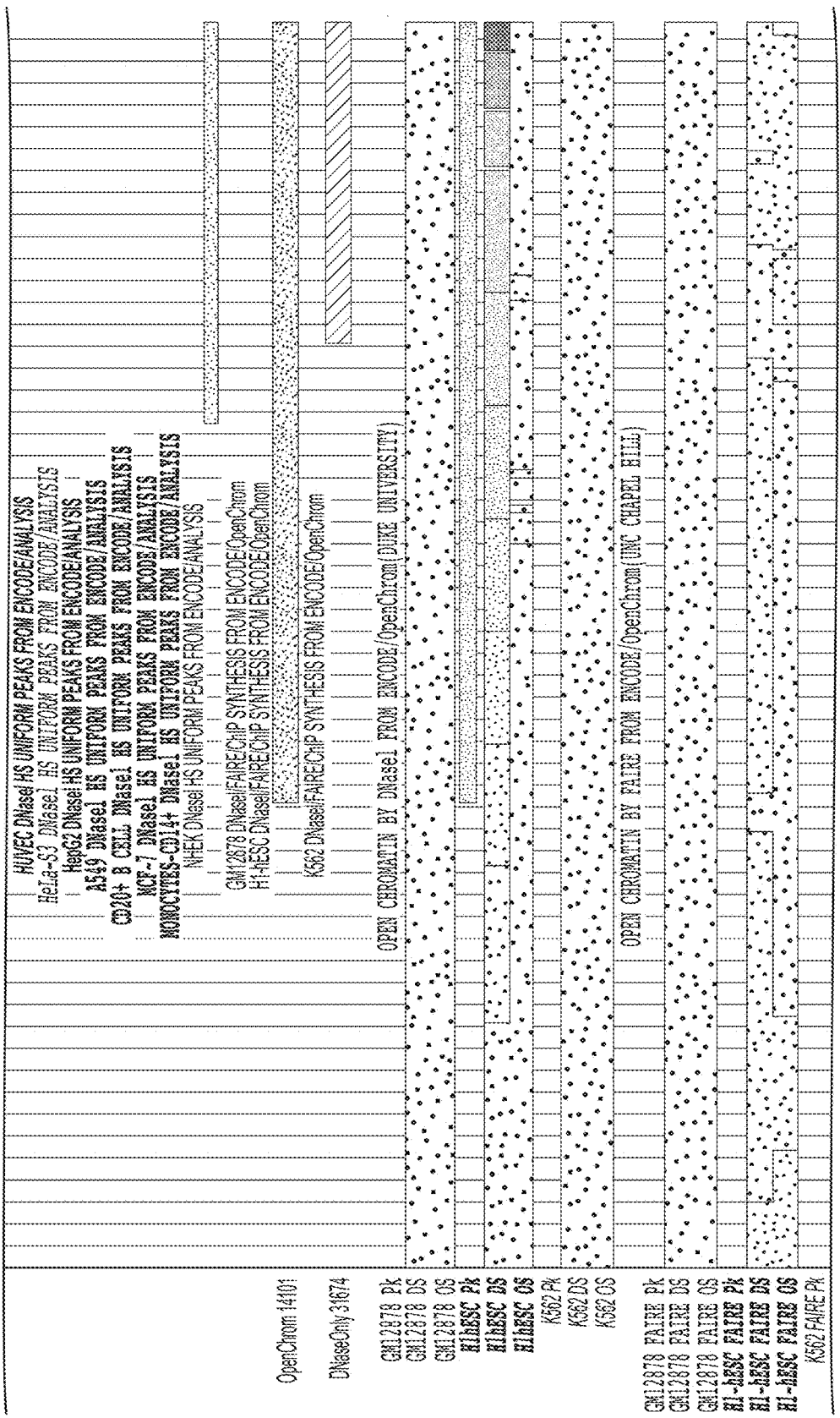
Figure 3:
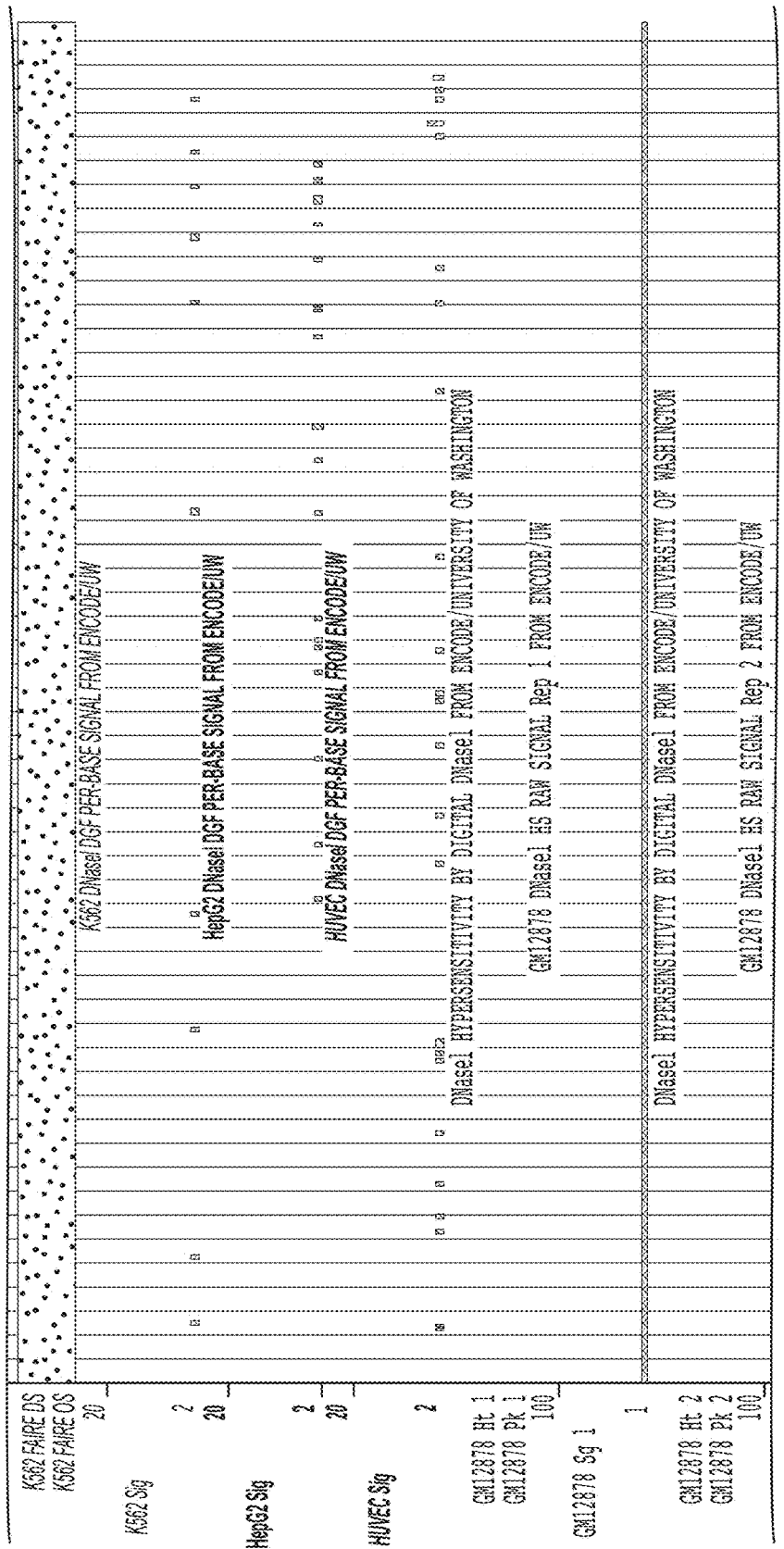
Figure 3:
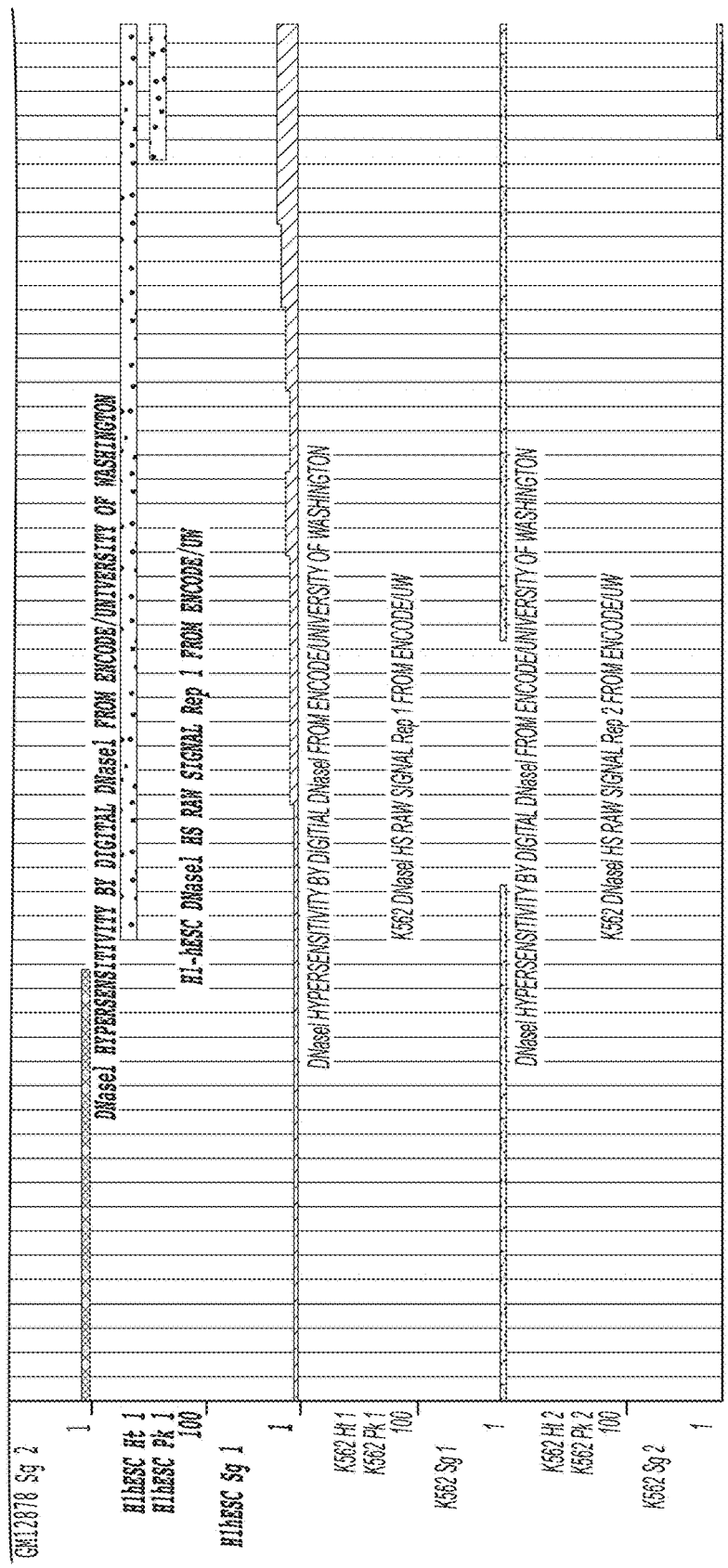

Results:

FXN was chosen as an exemplary gene for designing oligonucleotides because FXN is a housekeeping gene that is challenging to upregulate, and down-regulation of FXN is associated with the devastating disease Fredriech's ataxia (FRDA). Firstly, target euchromatin regions were identified within the FXN gene. These target euchromatin regions are determined to be regions of open chromatin where antisense RNAs are transcribed. DNAseI hypersensitivity data and CAGE data were combined as described in the above methods to identify the target euchromatin regions of FXN (FIGS. 2 and 3).

Figure 4:
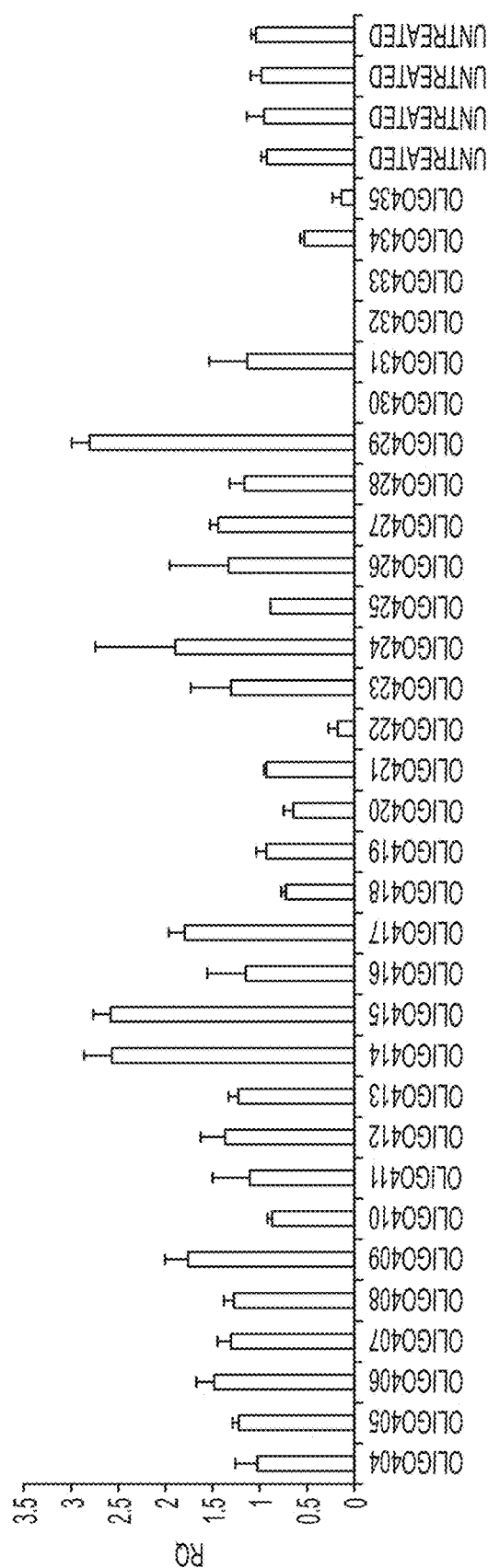
FIG. 4 is a graph showing levels of frataxin (FXN) mRNA after treatment of a cell line from a patient with FRDA with oligonucleotides complementary to a target euchromatin region of FXN.
Figure 5:
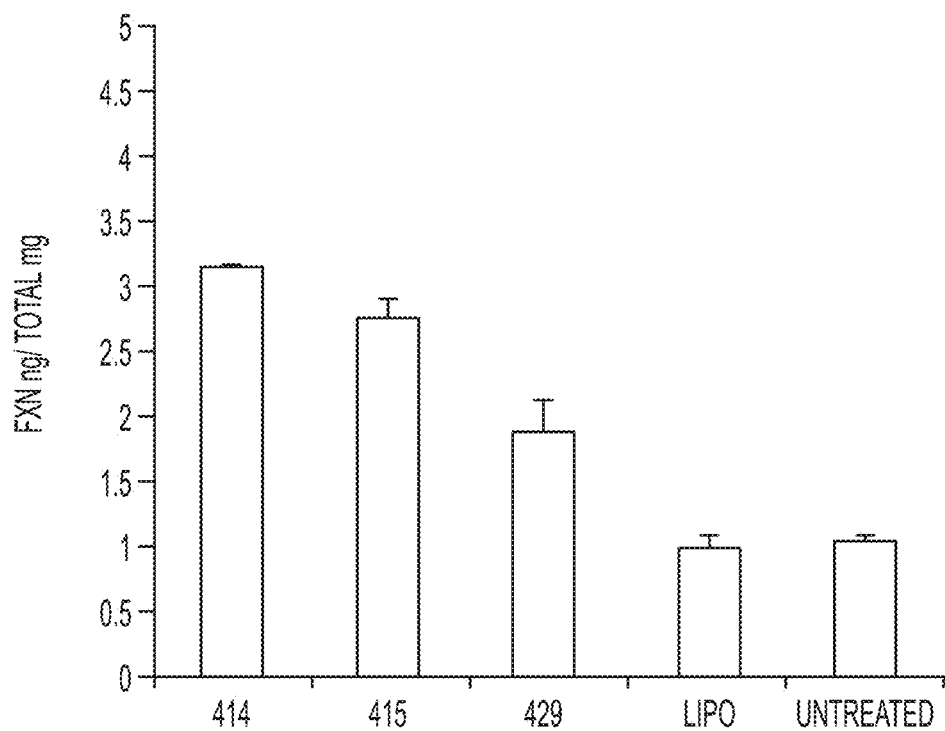
FIG. 5 is a graph showing levels of frataxin (FXN) protein after treatment of a cell line from a patient with FRDA with oligonucleotides complementary to a target euchromatin region of FXN.

The oligonucleotides were tested in a cell line obtained from a patient with FRDA. It was found that several oligonucleotides resulted in upregulation of FXN mRNA in the cell line (FIG. 4). Oligonucleotides 414, 415 and 429 showed the strongest level of upregulation of FXN mRNA. Oligonucleotides 414, 415 and 429 were then tested to determine if these oligonucleotides could also upregulate FXN protein levels. All three oligos caused upregulation of FXN protein (FIG. 5). These results indicate that oligonucleotides complementary to target euchromatin regions can modulate gene expression.

Figure 6:
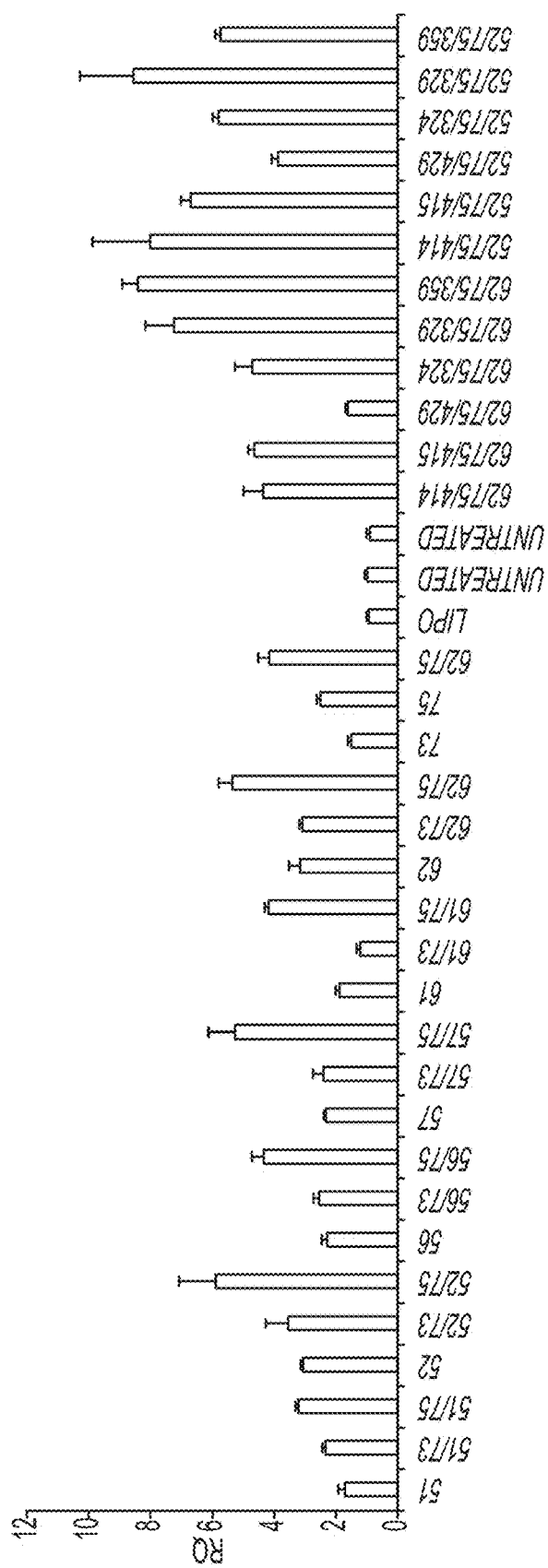
FIG. 6 is a graph showing levels of frataxin (FXN) mRNA after treatment of a cell line from a patient with FRDA with combinations of oligonucleotides complementary to a target euchromatin region of FXN and other FXN targeting oligonucleotides.

Lastly, oligos 414, 415 and 429 were tested in combination with other oligonucleotides designed to upregulate FXN. It was found that, in some cases, treatment of cells with a combination of oligonucleotides could increase the upregulation of FXN compared to treatment with a single oligonucleotide (FIG. 6). These results indicated that in some instances it may be useful to combine multiple different oligos that target different regions of FXN to further increase the upregulation of FXN.

Example 2. Further Experiments with Oligo 429

Figure 7:
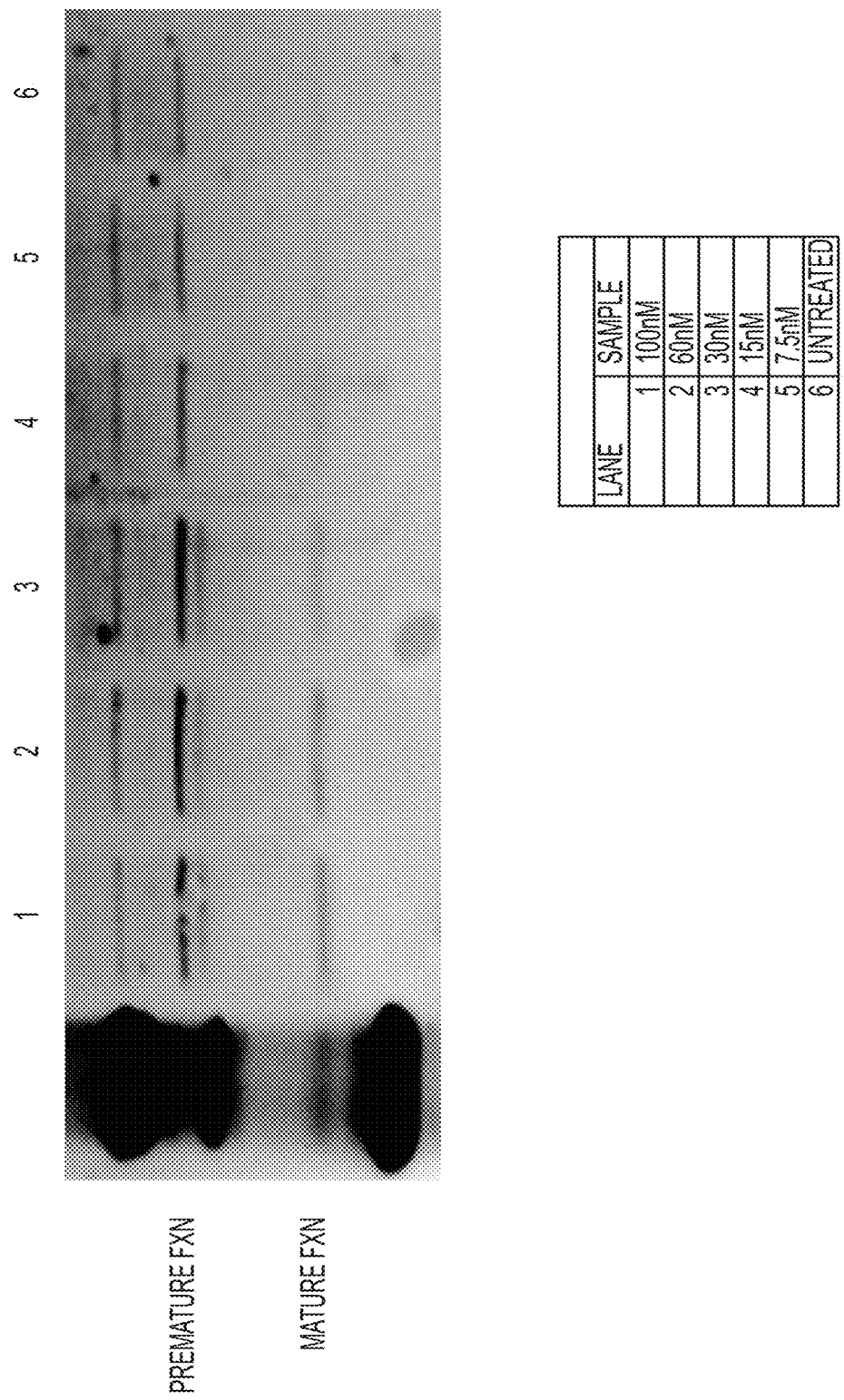
FIG. 7 is a photograph of a Western blot showing levels of FXN protein in cells treated with oligo 429 at various concentrations.

The FXN-429 oligo was transfected into GM03816 cells at 100 nM, 60 nM, 30 nM, 15 nM, and 7.5 nM. Protein lysates were collected at day4 and FXN protein levels were measured with the Abcam ab48281 antibody. Actin was used as the loading control. It was found that the 429 oligo caused upregulation of FXN protein in a dose-dependent manner (FIG. 7).

Example 3. Further Experiments with Oligo 414

Figure 9:
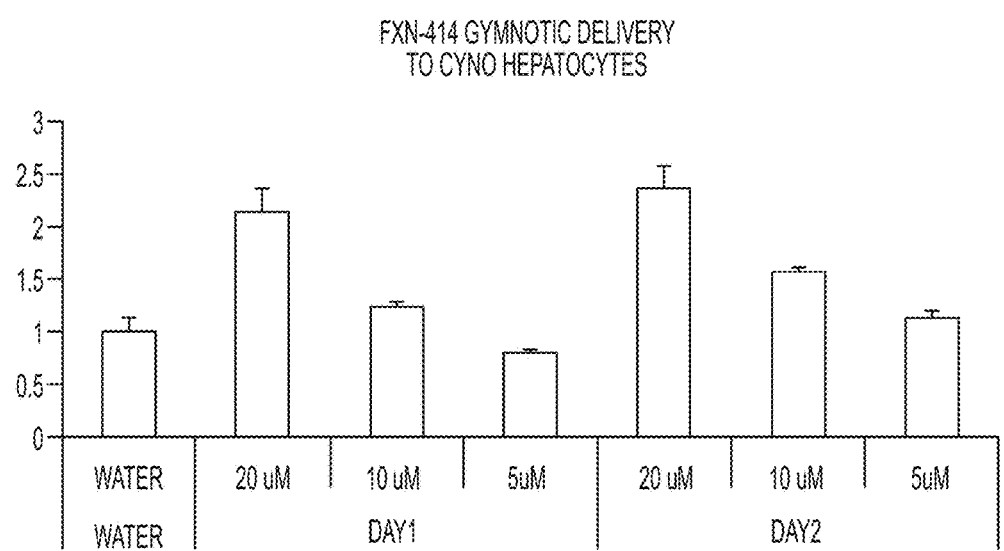
FIG. 9 is a graph showing FXN mRNA upregulation in cells treated with oligo 414.

The FXN-414 oligo was transfected gymnotically into hepatocytes derived from Cyno (cynomolgus monkey). Treatment concentrations were 20 uM, 10 uM and 5 uM. FXN RNA measurements were taken at days 1 and 2 post treatment. Dose-responsive FXN mRNA upregulation was observed with oligo 414 (FIG. 9).

Example 4. Further Experiments with Other Oligos

Further oligonucleotides were designed by combining various oligos with an oligo dT linker or designed to other hypersensitive regions. The origins of oligos were FXN-517m08: FXN415/429, FXN-518m02: FXN415/429. FXN-519m08 and 521m02 target another DNAse1 hypersensitive site in 3' UTR (in antisense direction). The sequences of the oligonucleotides are shown in the Table below.

TABLE 6

Further oligonucleotides

| SEQ ID NO | Oligo Name | Base Sequence | Gene Name | Organism | Formatted Sequence |
|---|---|---|---|---|---|
| 46 | FXN-517 m02 | GCAGGTTG AGACTGG | FXN | human | dGs;InaCs;dAs;InaGs;dGs;InaTs; dTs;InaGs;dAs;InaGs;dAs;InaCs; dTs;InaGs;dG-Sup |
| 47 | FXN-517 m08 | GCAGGTTG AGACTGG | FXN | human | dGs;InaCs;dAs;InaGs;dGs;InaTs; dTs;InaGs;dAs;InaGs;dAs;InaCs; dTs;InaGs;dG-Sup |
| 48 | FXN-518 m02 | AGGTTGAG ACTGGGT | FXN | human | dAs;InaGs;dGs;InaTs;dTs;InaGs; dAs;InaGs;dAs;InaCs;dTs;InaGs; dGs;InaGs;dT-Sup |
| 49 | FXN-519 m02 | GGAAAAAT TCCAGGA | FXN | human | dGs;InaGs;dAs;InaAs;dAs;InaAs; dAs;InaTs;dTs;InaCs;dCs;InaAs; dGs;InaGs;dA-Sup |
| 50 | FXN-519 m08 | GGAAAAAT TCCAGGA | FXN | human | InaGs;InaGs;InaAs;dAs;dAs;dAs; dAs;dTs;dTs;dCs;dCs;dAs;InaGs; InaGs;InaA-Sup |
| 51 | FXN-521 m02 | GAGGGAAA ATGAATT | FXN | human | dGs;InaAs;dGs;InaGs;dGs;InaAs; dAs;InaAs;dAs;InaTs;dGs;InaAs; dAs;InaTs;dT-Sup |

Figure 8:
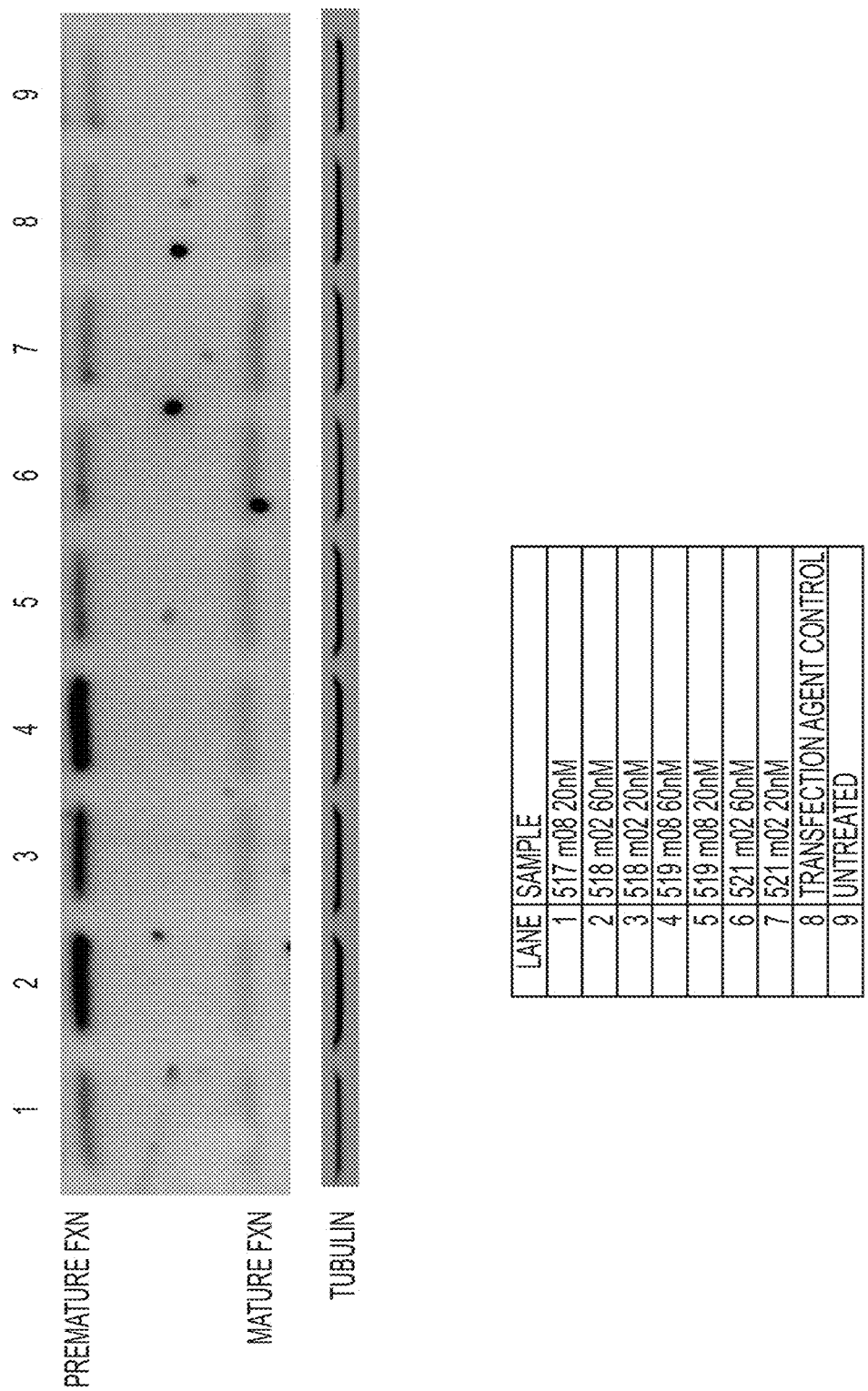
FIG. 8 is a photograph of a Western blot showing levels of FXN protein in cells treated with oligos 517m08, 518 m02, 519 m08 and 521 m02.

Oligos 517 m08, 518, 519 and 521 m08 oligos were transfected into GM03816 cells at 20 and 60 nanomolar concentrations. Protein lysates were collected at day4 and FXN protein levels were measured with the Abcam ab48281 antibody. Tubulin was used as the loading control. The strongest levels of FXN upregulation were observed with oligo 518 and 519 (FIG. 8).

Without further elaboration, it is believed that one skilled in the art can, based on the description provided herein, utilize the present invention to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method for increasing expression of a target gene in a cell, the method comprising:
   (a) determining that the target gene has a euchromatic region that is a DNase I hypersensitive site of up to 1000 bp in length that overlaps an intronic or 3' UTR sequence of the target gene, in which the antisense strand of the target gene comprises a target nucleotide sequence that i) encodes at least a portion of an RNA transcript and ii) is present within the euchromatic region;
   (b) following step (a), producing an oligonucleotide of 10 to 50 nucleotides in length that has a region of complementarity that is complementary with at least 5 contiguous nucleotides in the target nucleotide sequence, wherein the region of complementarity is of sufficient length to hybridize to the RNA transcript under physiological conditions and wherein the oligonucleotide is a mixmer that does not promote cleavage of the RNA transcript by RNase H in the cell; and
   (c) contacting the cell with the oligonucleotide produced in (b), thereby increasing expression of the target gene in the cell.

2. The method of claim 1, wherein the at least 5 contiguous nucleotides in the euchromatic region are on the antisense strand of the target gene.

3. The method of claim 1, wherein the RNA transcript is a long non-coding RNA.

4. The method of claim 1, further comprising determining that the euchromatic region of the target gene is enriched in lysine 4 methylated histone H3 or H4 compared to an appropriate control.

5. The method of claim 1, further comprising determining that the euchromatic region of the target gene is enriched in acetylated histone H3 or H4 compared to an appropriate control.

6. The method of claim 1, wherein the oligonucleotide is a single stranded oligonucleotide.

7. The method of claim 1, wherein the oligonucleotide comprises at least one modified intranucleoside linkage.

8. The method of claim 1, wherein at least one nucleotide comprises a 2' O-methyl.

9. A method for designing and evaluating an oligonucleotide, the method comprising:
  (a) determining that a target gene in a cell has a euchromatic region that is a DNase I hypersensitive site of up to 1000 bp in length that overlaps an intronic or 3' UTR sequence of the target gene, in which the antisense strand of the target gene comprises a target nucleotide sequence that i) encodes at least a portion of an RNA transcript and ii) is present within the euchromatic region;
  (b) following step (a), producing an oligonucleotide of 10 to 50 nucleotides in length that has a region of complementarity that is complementary with at least 5 contiguous nucleotides in the target nucleotide sequence, wherein the region of complementarity is of sufficient length to hybridize to the RNA transcript under physiological conditions and wherein the oligonucleotide is a mixmer that does not promote cleavage of the RNA transcript by RNase H in the cell; and
  (c) delivering to the cell the oligonucleotide produced in (b); and
  (d) evaluating expression of the target gene in the cell in response to delivery of the oligonucleotide.

10. A method for increasing expression of a target gene in a cell, the method comprising:
  contacting the cell with an oligonucleotide of 10 to 50 nucleotides in length that has a region of complementarity that is complementary with at least 5 contiguous nucleotides in a target nucleotide sequence,
  wherein the target gene has a euchromatic region that is a DNase I hypersensitive site of up to 1000 bp in length that overlaps an intronic or 3' UTR sequence of the target gene, wherein the antisense strand of the target gene comprises the target nucleotide sequence and the target nucleotide sequence i) encodes at least a portion of an RNA transcript and ii) is present within the euchromatic region, wherein the region of complementarity is of sufficient length to hybridize to the RNA transcript under physiological conditions, and wherein the oligonucleotide is a mixmer that does not promote cleavage of the RNA transcript by RNase H in the cell, thereby increasing expression of the target gene in the cell.

11. The method of claim 1, wherein the oligonucleotide is 10 to 20 nucleotides in length.

12. The method of claim 9, wherein the oligonucleotide is 10 to 20 nucleotides in length.

13. The method of claim 10, wherein the oligonucleotide is 10 to 20 nucleotides in length.

* * * * *

SEQUENCE LISTING

```
<160> NUMBER OF SEQ ID NOS: 51

<210> SEQ ID NO 1
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 1
tttttcattt tccctcctgg                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
tttttgtagg ctacccttta                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
tttttgaggc ttgttgcttt                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
tttttcatgt atgatgttat                                                   20

<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 5
aaagccttaa aaacc                                                        15

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
tcaggccaag acccc                                                        15

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 7
cccagcttca ttatg                                                        15
```

```
<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 8
aatgtgttgc ctcct                                                        15

<210> SEQ ID NO 9
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 9
aaaaagcaaa ataat                                                        15

<210> SEQ ID NO 10
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 10
ccaggaggga aaatg                                                        15

<210> SEQ ID NO 11
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 11
taaagggtag cctac                                                        15

<210> SEQ ID NO 12
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 12
aaagcaacaa gcctc                                                        15

<210> SEQ ID NO 13
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 13
ataacatcat acatg                                                        15

<210> SEQ ID NO 14
<211> LENGTH: 15
<212> TYPE: DNA
<213> ORGANISM: Artificial Sequence
<220> FEATURE:
<223> OTHER INFORMATION: Synthetic oligonucleotide
```

```
<400> SEQUENCE: 14
gatactatct tcctc                                                    15

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 15
atgggggacg gggca                                                    15

<210> SEQ ID NO 16
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 16
ggttgagact gggtg                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 17
agactgaaga ggtgc                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 18
cgggacggct gtgtt                                                    15

<210> SEQ ID NO 19
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 19
tctgtgtggg cagca                                                    15

<210> SEQ ID NO 20
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 20
aaagccttaa aaacc                                                    15
```

-continued

```
<210> SEQ ID NO 21
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 21
tcaggccaag acccc                                                       15

<210> SEQ ID NO 22
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 22
cccagcttca ttatg                                                       15

<210> SEQ ID NO 23
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 23
aatgtgttgc ctcct                                                       15

<210> SEQ ID NO 24
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 24
aaaaagcaaa ataat                                                       15

<210> SEQ ID NO 25
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 25
ccaggaggga aaatg                                                       15

<210> SEQ ID NO 26
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 26
taaagggtag cctac                                                       15

<210> SEQ ID NO 27
<211> LENGTH: 15
<212> TYPE: DNA
<213> ORGANISM: Artificial Sequence
<220> FEATURE:
<223> OTHER INFORMATION: Synthetic oligonucleotide
```

<400> SEQUENCE: 27
aaagcaacaa gcctc                                                    15

<210> SEQ ID NO 28
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 28
ataacatcat acatg                                                    15

<210> SEQ ID NO 29
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 29
gatactatct tcctc                                                    15

<210> SEQ ID NO 30
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 30
atgggggacg gggca                                                    15

<210> SEQ ID NO 31
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 31
ggttgagact gggtg                                                    15

<210> SEQ ID NO 32
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 32
agactgaaga ggtgc                                                    15

<210> SEQ ID NO 33
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 33
cgggacggct gtgtt                                                    15

```
<210> SEQ ID NO 34
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 34
tctgtgtggg cagca                                                          15

<210> SEQ ID NO 35
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 35
cgccctccag cgctg                                                          15

<210> SEQ ID NO 36
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 36
cgctccgccc tccag                                                          15

<210> SEQ ID NO 37
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 37
cgccctccag cgctgcc                                                        17

<210> SEQ ID NO 38
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 38
cgctccgccc tccagcc                                                        17

<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 39
cgccctccag cgctgggaaa cctc                                                24

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide
```

<400> SEQUENCE: 40
cgctccgccc tccagccaaa ggtc                                          24

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
tttttggggt cttggcctga                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
tttttaggag gcaacacatt                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
cggcgcccga gagtccacat                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
acggcggccg cagagtgggg                                               20

<210> SEQ ID NO 45
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 45
cctcaaaagc aggaataaaa aaaata                                        26

<210> SEQ ID NO 46
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 46
gcaggttgag actgg                                                    15

```
<210> SEQ ID NO 47
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 47
gcaggttgag actgg                                                    15

<210> SEQ ID NO 48
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 48
aggttgagac tgggt                                                    15

<210> SEQ ID NO 49
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 49
ggaaaaattc cagga                                                    15

<210> SEQ ID NO 50
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 50
ggaaaaattc cagga                                                    15

<210> SEQ ID NO 51
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 51
gagggaaaat gaatt                                                    15
```